US007465852B2

(12) United States Patent
Sewalt et al.

(10) Patent No.: US 7,465,852 B2
(45) Date of Patent: Dec. 16, 2008

(54) COMPOSITIONS AND METHODS FOR ALTERING THE DISULFIDE STATUS OF PROTEINS

(75) Inventors: Vincent Sewalt, West Des Moines, IA (US); Craig Hastings, Perry, IA (US); Robert Meeley, Des Moines, IA (US); Sabine Susanne Hantke, Cologne (DE); Rudolf Jung, Des Moines, IA (US); John D. Everard, Wilmington, DE (US); Stephen M. Allen, Wilmington, DE (US)

(73) Assignees: Pioneer Hi-Bred International, Inc., Des Moines, IA (US); E.I. du Pont de Nemours and Company, Wilmington, DE (US)

( * ) Notice: Subject to any disclaimer, the term of this patent is extended or adjusted under 35 U.S.C. 154(b) by 308 days.

(21) Appl. No.: 11/195,459

(22) Filed: Aug. 2, 2005

(65) Prior Publication Data
US 2005/0278803 A1 Dec. 15, 2005

Related U.S. Application Data

(62) Division of application No. 10/005,429, filed on Dec. 3, 2001, now Pat. No. 7,009,087.

(60) Provisional application No. 60/250,703, filed on Dec. 1, 2000.

(51) Int. Cl.
C12N 15/29 (2006.01)
C12N 15/82 (2006.01)
C12N 15/87 (2006.01)
C12N 5/04 (2006.01)
A01H 1/00 (2006.01)
A01H 5/10 (2006.01)

(52) U.S. Cl. ............... 800/298; 536/23.1; 536/23.6; 435/320.1; 435/410; 435/419; 800/287; 800/320.1; 800/314; 800/278; 800/290

(58) Field of Classification Search ............... 536/23.1, 536/23.6; 435/320.1, 410, 419; 800/298, 800/278, 290, 287, 320.1
See application file for complete search history.

(56) References Cited

U.S. PATENT DOCUMENTS

| 4,849,346 | A | 7/1989 | Wood et al. | |
|---|---|---|---|---|
| 4,904,602 | A | 2/1990 | Pigiet et al. | |
| 5,646,016 | A | 7/1997 | McCoy et al. | |
| 5,792,506 | A | 8/1998 | Buchanan et al. | |
| 5,952,034 | A | 9/1999 | Buchanan et al. | |
| 6,833,493 | B2 * | 12/2004 | Cho et al. ............... | 800/295 |
| 2002/0088025 | A1 | 7/2002 | Moloney et al. | |
| 2003/0135878 | A1 | 7/2003 | Cho et al. | |
| 2003/0150010 | A1 | 8/2003 | Cho et al. | |

FOREIGN PATENT DOCUMENTS

| EP | 0 208 539 A2 | 1/1987 |
|---|---|---|
| EP | 0 672 127 B1 | 9/1995 |
| EP | 0 768 382 A2 | 4/1997 |
| EP | 0 853 088 A2 | 7/1998 |
| EP | 0 863 154 A1 | 9/1998 |
| WO | WO 95/01425 A1 | 1/1995 |
| WO | WO 96/03505 A1 | 2/1996 |
| WO | WO 99/20122 A1 | 4/1999 |
| WO | WO 00/14239 A2 | 3/2000 |
| WO | WO 00/36126 A1 | 6/2000 |
| WO | WO 00/58352 A2 | 10/2000 |
| WO | WO 00/58453 A2 | 10/2000 |
| WO | WO 01/98509 A2 | 12/2001 |
| WO | WO 02/50289 A1 | 6/2002 |

OTHER PUBLICATIONS

Bowie et al, Science 247:1306-1310, 1990.*
McConnell et al, Nature 411 (6838):709-713, 2001.*
Besse, I., et al., "Thiocalsin: A Thioredoxin-Linked, Substrate-Specific Protease Dependent on Calcium," *Proc. Natl. Acad. Sci. USA*, 1996, pp. 3169-3175, vol. 93.
Boisen, S., and J.A. Fernández, "Prediction of the Total Tract Digestibility of Energy in Feedstuffs and Pig Diets by In Vitro Analyses," *Animal Feed Science and Technology*, 1997, pp. 277-286, vol. 68, Elsevier Science B.V.
Bowie, J., et al., "Deciphering the Message in Protein Sequences: Tolerance to Amino Acid Substitutions," *Science*, 1990, pp. 1306-1310, vol. 247.
Bréhélin, C., et al., "Characterization of Determinants for the Specificity of *Arabidopsis* Thioredoxins h in Yeast Complementation," *The Journal of Biological Chemistry*, 2000, pp. 31641-31647, vol. 275(41), The American Society for Biochemistry and Molecular Biology, Inc., USA.
Brugidou, C., et al., "The *Nicotiana tabacum* Genome Encodes Two Cytophasmic Thioredoxin Genes Which Are Differently Expressed," *Mol. Gen. Genet.*, 1993, pp. 285-293, vol. 238, Springer-Verlag.
Buchanan, B., et al., "Thioredoxin-Linked Mitigation of Allergic Responses to Wheat," *Proc. Natl. Acad. Sci. USA*, 1997, pp. 5372-5377, vol. 94, The National Academy of Sciences, USA.
Colliver, S., et al., "Differential Modification of Flavonoid and Isoflavonoid Biosynthesis with an Antisense Chalcone Synthase Construct in Transgenic *Lotus corniculatus*," *Plant Molecular Biology*, 1997, pp. 509-522, vol. 35.

(Continued)

*Primary Examiner*—Stuart F. Baum
(74) *Attorney, Agent, or Firm*—Alston & Bird LLP

(57) ABSTRACT

Compositions and methods for the alteration of the disulfide status of plant proteins are provided. Novel nucleotide molecules, comprising nucleotide sequences for thioredoxin h and NADPH-thioredoxin reductase, and the proteins encoded thereby are provided. The nucleotide sequences can be used to transform plants alone or in combination with other sequences, such as sequences encoding NADPH generating enzymes, to manipulate the thioredoxin h system and alter the protein disulfide status in plants. Transformed plants, plant cells, plant tissues, seed and grain are provided.

27 Claims, 3 Drawing Sheets

OTHER PUBLICATIONS

Dai, S., et al., "Crystal Structure of *Arabidopsis thaliana* NADPH Dependent Thioredoxin Reductase at 2.5 Å Resolution," *J. Mol. Biol.*, 1996, pp. 1044-1057, vol. 264, Academic Press Limited.

Fahrendorf, T., et al., "Stress Responses in Alfalfa (*Medicago sativa* L.) XIX. Transcriptional Activation of Oxidative Pentose Phosphate Pathway Genes at the Onset of the Isoflavonoid Phytoalexin Response," *Plant Molecular Biology*, 1995, pp. 885-900, vol. 28, Kluwer Academic Publishers, Belgium.

Gautier, M., et al., "Characterization of Wheat Thioredoxin *h* cDNA and Production of an Active *Triticum aestivum* Protein in *Escherichia coli*," *Eur. J. Biochem.*, 1998, pp. 314-324, vol. 252, FEBS.

Graeve, K., et al., "Purification, Characterization, and cDNA Sequence of Glucose-6-Phosphate Dehydrogenase from Potato (*Solanum tuberosum* L.)," *The Plant Journal*, 1994, pp. 353-361, vol. 5(3), BIOS Scientific Publishers Ltd., Blackwell Scientific Publications Ltd., and the Society for Experimental Biology, USA.

Ishiwatari, Y., et al., "Thioredoxin h is One of the Major Proteins in Rice Phloem Sap," *Planta*, 1995, pp. 456-463, vol. 195, Springer-Verlag.

Jacquot, J., et al., "*Arabidopsis thaliana* NAPHP Thioredoxin Reductase: cDNA Characterization and Expression of the Recombinant Protein in *Escherichia coli*," *J. Mol. Biol.*, 1994, pp. 1357-1363, vol. 235, Academic Press Limited.

Jacquot, J., et al., "Analysis and Manipulation of Target Enzymes for Thioredoxin Control," *Methods in Enzymology*, 1995, pp. 240-253, vol. 252, Academic Press, Inc.

Jiao, J., et al., "Effect of Thioredoxin-Linked Reduction on the Activity and Stability of the Kunitz and Bowman-Birk Soybean Trypsin Inhibitor Proteins," *J. Agric. Food Chem.*, 1992, pp. 2333-2336, vol. 40, American Chemical Society, USA.

Jiao, J., et al., "Thioredoxin-Linked Changes in Regulatory Properties of Barley Alpha-Amylase/Subtilisin Inhibitor Protein," *Plant Physiol. Biochem.*, 1993, pp. 799-804, vol. 31(6), Gautier-Villars.

Kobrehel, K., et al., "Role of the NADP/Thioredoxin System in the Reduction of Alpha-Amylase and Trypsin Inhibitor Proteins," *The Journal of Biological Chemistry*, Aug. 1991, pp. 16135-16140, vol. 266(24), The American Society for Biochemistry and Molecular Biology, Inc., USA.

Kobrehel, K., et al., "Specific Reduction of Wheat Storage Proteins by Thioredoxin *h*," *Plant Physiol.*, 1992, pp. 919-924, vol. 99.

Lozano, R., et al., "New Evidence for a Role for Thioredoxin h in Germination and Seedling Development," Planta, 1996, pp. 100-106, vol. 200, Springer-Verlag GmbH & Co. KG, Berlin.

McConnell, J., et al., "Role of *PHABULOSA* and *PHAVOLUTA* in Determining Radial Patterning in Shoots," *Nature*, 2001, pp. 709-713, vol. 411.

Meyer, Y., et al., "Plant Thioredoxins and Glutaredoxins: Identity and Putative Roles," Trends in Plant Science, 1999, pp. 388-394, vol. 4(10), Elsevier Applied Science, United Kingdom.

Montgomery, M. and A. Fire, "Double-Stranded RNA as a Mediator in Sequence-Specific Genetic Silencing and Co-Suppression," *TIG*, 1998, pp. 255-258, vol. 14.

Mouaheb, N., et al., "In Vivo Functional Discrimination Between Plant Thioredoxins by Heterologous Expression in the Yeast *Saccharomyces cerevisiae*," Proc. Natl. Acad. Sci. USA, 1998, pp. 3312-3317, vol. 95, The National Academy of Sciences, USA.

Rivera-Madrid, R., et al., "Nucleotide Sequence of a cDNA Clone Encoding an *Arabidopsis thaliana* Thioredoxin h," Plant Physiol., 1993, pp. 327-328, vol. 102.

Rivera-Madrid, R., et al., "Evidence for Five Divergent Thioredoxin h Sequences in *Arabidopsis thaliana*," Proc. Natl. Acad. Sci. USA, 1995, pp. 5620-5624, vol. 92.

Verdoucq, L., et al., "In Vivo Characterization of a Thioredoxin h Target Protein Defines a New Peroxiredoxin Family," The Journal of Biological Chemistry, 1999, pp. 19714-19722, vol. 274, The American Society for Biochemistry and Molecular Biology, Inc., USA.

Wong, J., et al., "Thioredoxin and Bread Wheat," Cereal Chemistry, 1993, pp. 113-114, vol. 70(1), American Association of Cereal Chemists, Inc., USA.

Zhang, P., et al., "Thioredoxin Peroxidase Is a Novel Inhibitor of Apoptosis with a Mechanism Distinct from That of Bcl-2," The Journal of Biological Chemistry, 1997, pp. 30615-30618, vol. 272(49), USA.

GenBank Report for Accession No. D26547, Direct Submission on Jan. 18, 1993.

GenBank Report for Accession No. D21836, Direct Submission on Oct. 28, 1993.

GenBank Report for Accession No. AI834553, Direct Submission on Jul. 14, 1999.

GenBank Report for Accession No. D49132, Direct Submission on Mar. 9, 1995.

GenBank Report for Accession No. AJ001903, Direct Submission on Oct. 1, 1997.

GenBank Report for Accession No. AF051206, Direct Submission on Feb. 27, 1998.

GenBank Report for Accession No. AA979723, Direct Submission on May 26, 1998.

GenBank Report for Accession No. S44026, Direct Submission on Nov. 6, 1998.

GenBank Report for Accession No. AI670386, Direct Submission on May 14, 1999.

GenBank Report for Accession No. AI738120, Direct Submission on Jun. 16, 1999.

GenBank Report for Accession No. AW172111, Direct Submission on Nov. 15, 1999.

GenBank Report for Accession No. AW313252, Direct Submission on Jan. 24, 2000.

GenBank Report for Accession No. AC002329 AE002093, Direct Submission on Mar. 9, 2000.

GenBank Report for Accession No. AW562878, Direct Submission on Mar. 10, 2000.

GenBank Report for Accession No. AW679524, Direct Submission on Apr. 14, 2000.

GenBank Report for Accession No. AW681036, Direct Submission on Apr. 14, 2000.

* cited by examiner

COMPOSITIONS AND METHODS FOR ALTERING THE DISULFIDE STATUS OF PROTEINS

CROSS-REFERENCE TO RELATED APPLICATIONS

This application is a division of U.S. application Ser. No. 10/005,429 filed Dec. 3, 2001, now U.S. Pat. No. 7,009,087 issued Mar. 7, 2006, which claims the benefit of U.S. Provisional Application No. 60/250,703, filed Dec. 1, 2000, both of which are hereby incorporated herein in their entirety by reference.

FIELD OF THE INVENTION

The present invention relates to the field of plant molecular biology, particularly to the isolation of genes. The invention further relates to the use of the genes to improve crop plants.

BACKGROUND OF THE INVENTION

The United States is the world-wide leader in corn (maize) production, producing about twice as much corn as the second-ranked producer. By far, corn is the most important grain crop in the United States. According to USDA estimates, corn ranked first in 1998 in acreage accounting for 24 percent of all crop acres in the United States. Nearly twice as many bushels of corn are produced per year in the U.S. than are produced for any other grain crop.

Despite the large amount of corn produced in the United States, only a minor portion of this corn is used directly for human consumption. The impact of corn on the American diet, however, is certainly not insignificant. Indirectly, corn has a profound impact on the American diet. Because the majority of the United States corn crop is used as feed for livestock, much of the meat consumed in the United States comes from animals that have been fed a diet that includes corn. In addition, corn also impacts the American diet in products that are come from the processing or refining of corn kernels. Key among the food products derived from corn refining are starch, corn oil and corn syrup. Produced from the hydrolysis of starch, corn syrup is used primarily as a sweetener, often replacing cane sugar (sucrose) in food and beverage products. While a variety of corn syrups may be produced from corn starch, the most popular form for use as a sweetener is high-fructose corn syrup. Over the last decade, high-fructose corn syrup has become the favored sweetener for many food products including most of the leading soft drinks.

Because of the importance of corn, plant breeders and other agricultural scientists have focused a great deal of their efforts on improving corn germplasm. While traditional efforts to improve corn have provided cultivars with improved yield potential and enhanced disease resistance, new approaches involving genetic engineering have already proven successful and have provided the corn producer new varieties with increased resistance to herbicides and insects. Other corn improvement efforts have focused on improving grain quality traits such as amino acid content, starch composition, oil content and composition, phytate content, and characteristics which affect corn refining processes such as wet milling. While traditional plant breeding approaches will continue to be relied upon for corn improvement, genetic engineering promises to provide novel approaches that can increase the rate of new cultivar development.

SUMMARY OF THE INVENTION

Compositions and methods for the alteration of the disulfide status of plant proteins are provided. The compositions comprise novel nucleotide molecules comprising nucleotide sequences for thioredoxin h and NADPH-thioredoxin reductase. The compositions can be used to transform plants alone or in combination with other sequences, such as sequences encoding NADPH generating enzymes, to manipulate the thioredoxin h system and alter the protein disulfide status in plants.

Transformed plants, plant cells, plant tissues, seed and grain are provided. Transformed plants of the invention find use in methods for improving grain or seed characteristics including, but not limited to, hardness, wet-milling efficiency, dry milling efficiency, dry grind ethanol production efficiency and digestibility.

Expression cassettes comprising sequences of the invention are provided. Isolated proteins encoded by the nucleotide sequences of the invention are also provided.

DETAILED DESCRIPTION OF THE INVENTION

Figure 1:
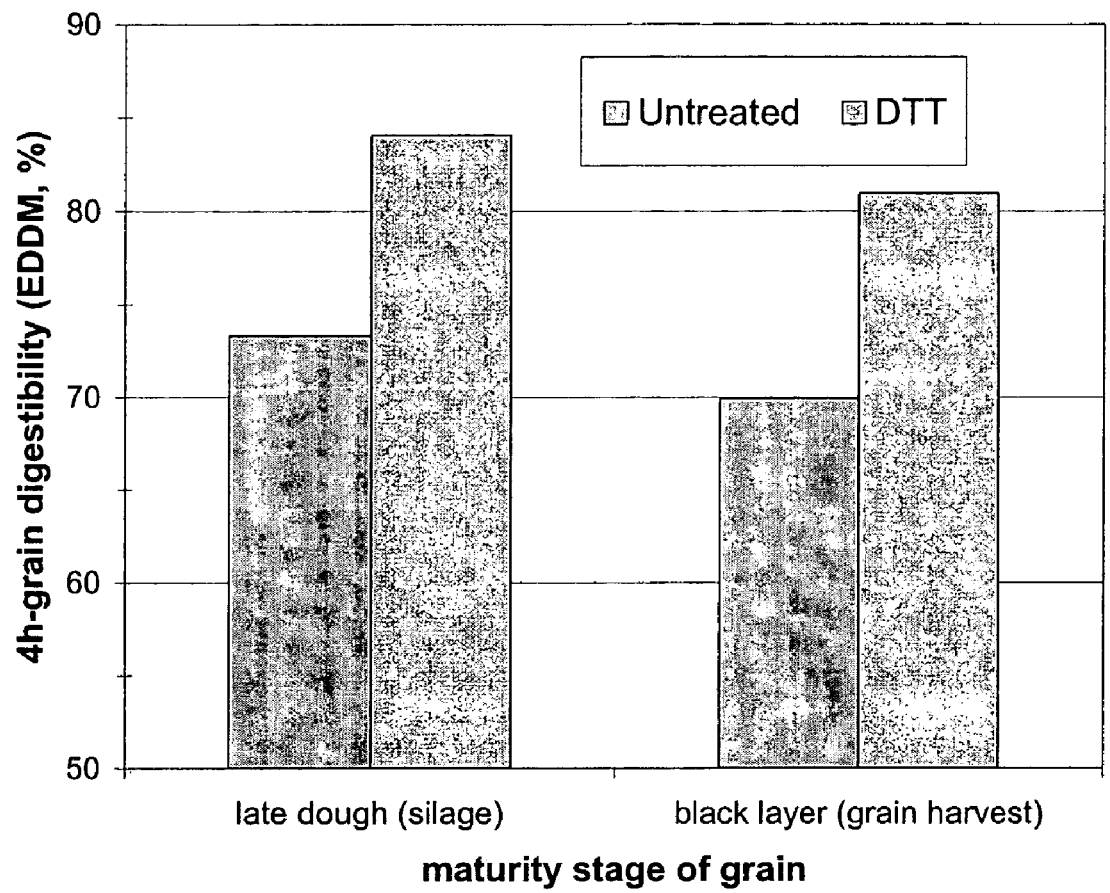
FIG. 1 is a graphical depiction of the digestibility of maize kernels (grain) at the late dough stage and the black layer stage. The figure shows the improvement in grain and immature kernel dry matter digestibility as a result of treatment with reducing agent. Digestibility was determined as enzyme digestible dry matter percent (EDDM %) with and without a dithiothreitol (DTT) pretreatment.

The invention is drawn to compositions and methods for altering disulfide status of proteins, particularly proteins in plants. The compositions and methods find use in improving the nutritional quality of plant proteins for use as food for humans and feed for livestock. Furthermore, the invention provides plants that possess traits such as, for example, grain that is easier to digest by both humans and livestock and grain that is improved for wet milling and other grain processing methods. As used herein, "grain" means the mature seed produced by commercial growers for purposes other than reproducing the species and/or immature seed as an integral part of whole plant corn harvested for silage.

By "disulfide status" is intended the portion of cysteine residues within a protein which participate in disulfide bonds or disulfide bridges. Such disulfide bonds can be formed between the sulfur of a first cysteine residue and the sulfur of a second cysteine residue. It is recognized that such first and second cysteine residues can occur as part of a single polypeptide chain, or alternatively, can occur on separate polypeptide chains.

Thioredoxins are important regulators of disulfide status and folding patterns of enzymes and other proteins. The chloroplastic thioredoxins (m and ƒ) function as regulators of enzymes of photosynthesis and the pentose phosphate cycle. Thioredoxin h (TRX), which is localized in cytoplasm, plays a central role in initiating the mobilization of nitrogen and carbon during seed germination (Kobrehel et al., 1992; Lozano et al., 1996). Activation of thioredoxin h requires reduction of its own intramolecular disulfide bridge by a specific, NADPH-dependent thioredoxin reductase (NTR). The NTR, in turn, requires adequate reducing equivalents in the form of NADPH. The cytosolic forms of 6-phosphogluconate dehydrogenase (6PGDH) and glucose 6-phosphate dehydrogenase (G6PDH) have been implicated to provide the necessary NADPH to drive NTR and TRX activity during germination of wheat (Lozano et al., 1996).

The invention provides isolated nucleotide molecules comprising nucleotide sequences encoding thioredoxins and thioredoxin reductases. Also provided are isolated proteins encoded by such nucleotide sequences. The nucleotide sequences find use in methods for altering the disulfide status of proteins in a plant, particularly proteins in maize plants, most particularly proteins in maize kernels. The methods find use in altering the disulfide status of storage proteins, in improving the digestibility of grain by humans and livestock, in reducing nitrogen excretion into the environment, in altering the hardness of seed and grain and in increasing the efficiency of the wet-milling, steam flaking and grinding of maize kernels.

Methods for altering the disulfide status of proteins are provided. The methods comprise transforming a plant with at least one nucleotide construct comprising at least a portion of at least one nucleotide sequence of the invention. If desired, the nucleotide construct may additionally comprise an operably linked promoter that drives expression in the plant of interest. Such a nucleotide construct can be used to increase the expression of a thioredoxin and/or thioredoxin reductase in a plant. By increasing the expression of enzymes that are involved in the reduction of protein disulfides, the disulfide bridges in a plant can be decreased, rearranged or both.

By "rearranged" is intended that the one of the participating sulfurs in a disulfide bond is changed. For example, a pair of disulfide bonds with the first bond between the sulfur of a first cysteine moiety and the sulfur of a second cysteine moiety and the second bond between the sulfur of a third cysteine moiety and the sulfur of a fourth cysteine moiety, is "rearranged" to a new first disulfide bond between the sulfur of the first cysteine moiety and the sulfur of the third cysteine residue and a new second disulfide bond the sulfur of the second cysteine moiety and the sulfur of the fourth cysteine residue.

Among the many applications of cereal protein disulfide reduction and/or re-arrangement by the methods of the present invention are the strengthening of wheat dough and improvement of baked goods, neutralization of food allergens, and increased digestibility of proteins. Altering the disulfide status of proteins in a plant or part thereof can provide improved food sources for humans and livestock by improving the digestibility of the plant tissue. The methods of the invention can improve protein digestibility and also increase starch utilization by increasing the release of starch granules from grain during digestion.

The nucleotide constructs of the invention comprise at least a portion of a nucleotide sequence of the invention. The nucleotide construct of the invention may additionally comprise at least one promoter that drives expression in a plant. Preferred promoters include those that drive gene expression in seeds, particularly during seed development. More preferred promoters are the promoters of the 19 KD α-zein gene and the 70 KD heat-shock gene. Another preferred promoter is the promoter for the 27 KD gamma-zein gene. A nucleotide construct of the invention comprises at least one nucleotide sequence of the invention. Preferably, such a nucleotide construct additionally comprises an operably linked promoter that drives expression in a plant. If desired, two or more of such nucleotide constructs may be linked or joined together to form one polynucleotide molecule, and such a polynucleotide may be used to transform a plant. For example, a nucleotide construct comprising a nucleotide sequence encoding a thioredoxin h (SEQ ID NOs: 1, 3, 5, 7, 9, 11, 13, 15, 17, or 18) and a nucleotide construct comprising a nucleotide sequence encoding a thioredoxin reductase (SEQ ID NOs:20, 22, and 24) may be linked to form a single polynucleotide molecule which can be used to transform a plant.

Depending on the desired outcome, a plant can be transformed with a single thioredoxin or thioredoxin reductase nucleotide sequence of the invention. Alternatively, a plant can be transformed with a thioredoxin nucleotide sequence and a thioredoxin reductase nucleotide sequence. The two nucleotide sequences can be part of the same nucleotide construct or on different nucleotide constructs. Each of the separate nucleotide sequences can be operably linked to a promoter that drives expression in a plant. If separate nucleotide constructs are employed for the thioredoxin nucleotide thioredoxin reductases nucleotide sequences, two individual plants may be transformed with the nucleotide constructs, and the plants crossed to produce progeny having the desired genotype of both the thioredoxin and thioredoxin reductase nucleotide sequences.

The reduction of disulfides in a plant depends on reducing equivalents, such as for example, NADH and NADPH. If desired, a plant can also be transformed with one or more additional nucleotide sequences encoding NADPH-generating enzymes to increase the biosynthesis of NADPH. Such enzymes include, but are not limited to, 6-phosphogluconate dehydrogenase and glucose-6-phosphate dehydrogenase. Any nucleotide sequence encoding 6-phosphogluconate dehydrogenase or glucose-6-phosphate dehydrogenase can be employed in the methods of the present invention including nucleotide sequences encoding plastidic and cytosolic forms of such enzymes. Such nucleotide sequences can be operably linked to a promoter that drives expression in a plant and, if necessary, can be operably linked to a plastid-targeting sequence. Alternatively, a plastid-targeting signal can be removed from the nucleotide sequence of a plastid-localized NADPH-generating enzyme to change the localization of such an enzyme to the cytosol. Nucleotide sequences encoding 6-phosphogluconate dehydrogenase include, but are not limited to, GenBank Accession Nos. AF061838, AF061837 and U18239, and DDBJ Accession No. AB007907. Nucleotide sequences encoding glucose-6-phosphate dehydrogenase include, but are not limited to, GenBank Accession Nos. AF012861, AF012862, AF012863, and U18238, and EMBL Accession Nos. AJ001359, AJ001769, AJ001770, AJ001771, AJ001772, X74421, X83923, X84229 and X84230.

The methods of the present invention can be employed to alter the disulfide status of proteins in any plant or part thereof. The preferred plants of the invention are cereals including, but not limited to, maize, wheat, rice, barley, rye, sorghum, oats and millet. Some methods of the invention involve altering the disulfide status of proteins in grain and other parts of a plant that may be subjected to post-harvest processing or can be used as food source for humans, livestock and other animals.

In one embodiment, the invention provides cereal plants that produce grain, particularly maize kernels, that are improved for use in industrial processing by methods such as, for example, wet milling. The corn wet-milling process requires steeping with large amounts of sulfur-reducing chemicals (e.g., sulfur dioxide) to reduce the disulfides present in corn kernels and thereby maximize starch yield (Hoseney, R. C. 1994. Principles of Cereal Science and Technology, second edition. Am. Assoc. Cereal Chemists, St. Paul, Minn.). By decreasing the disulfide status of grain, the amount of sulfur-reducing chemicals used in wet milling can be decreased.

Furthermore, a reduction in the amount of reducing chemicals or agents can provide other benefits. The use in wet mills of odorous chemicals such as sulfur dioxide and bisulfite requires extensive precautions and poses significant environmental problems. (May, J. B. Wet milling: process and products. In: Corn: Chemistry and Technology. Watson, S. A., and Ramstad, P. E. (Eds.). Am. Assoc. Cereal Chemists, St. Paul, Minn. pp.377-397.) For example, decreasing the amount of reducing agents required for wet milling can provide an environmental benefit in that the resulting process water will contain a lower level of the reducing chemicals, thereby lowering the costs of decontamination or disposal of the spent process water. Another benefit is that a lower level of reducing chemicals in the process water can improve the recovery of valuable components of kernels that otherwise would be destroyed, denatured, or otherwise negatively impacted by the presence of a standard level of reducing chemicals in the process water. Such components include, but are not limited to, vitamins, cofactors and proteins. The wet miller may also obtain by-products of the wet milling process, such as corn gluten feed and corn gluten meal, with improved digestibility as a result of the invention. Thus, the wet miller can obtain new sources of revenue from the recovery of such components and by-products.

Additionally, decreasing the rigidity of the continuous protein matrix late in kernel development can reduce the amount of energy required to grind cereal grain or in steam-flaking corn or sorghum, as well as increase the efficiency of these processes. The response to steam-flaking of corn and sorghum grain is negatively correlated with protein disulfide content (Blackwood, R. B., and Richardson, C. R. 1994. Steam-flaking and grain source effects on disulfide bonds in grain sorghum and corn. In: Animal Science and Food Technology Research Report 1994. Agricultural Sciences and Natural Resources Technical Report No. T-5-342. Texas Tech University, Lubbock, Tex., pp. 49-51). For corn or sorghum with lower degree of protein disulfide cross-linking, the extent of disulfide rearrangements during processing is reduced, which allows for higher and more uniform response to steam-flaking, and which can be expected to reduce the energy required in steam-flaking, as well as in grinding. Furthermore, the feed quality of the grain will be improved by reduced endosperm rigidity, allowing for reduced particle size of ground corn under fixed grinding regime.

In addition, dry grind ethanol production is improved by the use of the invention described herein. This improvement may be due to increased fermentable starch available for ethanol production. Dry grind ethanol production may also be improved as a result of the increased digestibility, and therefore increased value, of fermentation by-products such spent brewer's grain or thin stillage.

A cereal plant, particularly a maize plant, can be transformed with a nucleotide construct of the invention to reduce protein disulfides during kernel development. To reduce kernel hardness, the plant can be transformed with a nucleotide construct comprising a promoter that drives expression in the kernel during the later stages of grain fill and maturation. Overexpression of thioredoxin h and/or NADPH thioredoxin reductase at late stages of grain fill and maturation (e.g., 35-45 DAP) to chemically reduce intra- and inter-molecular disulfide bridges in endosperm proteins such as, for example, zeins, purothionins and glutenins, can decrease the rigidity of the continuous protein matrix. Such a modification to the kernel can, for example, improve feed quality by increasing digestibility. Protein digestibility of ground corn and sorghum is limited by protein disulfide crosslinking. (See Hamaker, B. R., Kirleis, A. W., Butler, L. G., Axtell, J. D., and Mertz, E. T. 1987. Improving the in vitro protein digestibility of sorghum with reducing agents. Proc. Natl. Acad. Sci. USA 84: 626-628). Hamaker et al. demonstrate that application of reducing agents to ground corn or sorghum improves protein digestibility. As shown in FIG. 1, Applicants have further determined that application of reducing agents to mature grain and immature kernels improves overall dry matter digestibility and starch digestibility. These findings apply to mature grain fed to monogastric and ruminant livestock, as well as to ruminant feed in the form of corn silage and high moisture corn. The latter two types of feed are minimally processed (e.g., not subjected to grinding), which allows reducing conditions to be maintained, whereby the reoxidation of sulfhydryl groups will be minimized. In corn silage, reducing conditions are actually promoted by exclusion of oxygen and rapid initiation of fermentative processes.

Additionally, decreasing the rigidity of the continuous protein matrix late in kernel development can reduce the amount of energy required to grind corn and/or improve feed quality by reducing the particle size of ground corn under fixed grinding regime. Decreasing the rigidity of the continuous protein matrix can also provide benefits for the processing of corn kernels by increasing the recovery of starch during wet milling and by reducing the need for chemical reductants during the steeping which precedes wet milling.

In an embodiment of the invention, a cereal plant, particularly a maize plant, is provided that produces kernels with increased starch content and an a softer protein texture. Such a plant comprises in its genome at least one nucleotide construct of the invention comprising a nucleotide sequence of the invention. Increased expression of thioredoxin and/or thioredoxin reductase at relatively early to mid-stages of grain fill (20-40 DAP) can delay the formation and re-arrangement of storage protein disulfides and reduce the hardness of corn kernels, with hardness of corn kernels determined by the industry standard Stenvert hardness test (see Pomeranz, Y., Czuchajowska, Z., Martin, C. R., and Lai, F. S. 1985. Determination of corn hardness by the Stenvert hardness tester. Cereal Chem. 62:108-112).

Yeast and mammalian thioredoxins are also implicated to protect cells from oxidative stress and inhibit apoptosis by activation of thioredoxin peroxidase (Zhang et al. (1997) *J. Biol. Chem.* 272:30615-30618; Verdouca et al. (1999) *J. Biol. Chem.* 274:19714-19722). If thioredoxin h is similarly involved in regulation of apoptosis in plants and, more specifically, developing seed, it can be employed to delay the maturation of corn endosperm. This delay in maturation may result in higher starch yield and may also alter the degree to which protein disulfides are re-formed during maturation and dry-down of the kernel, and thus provide increased starch content and a softer protein texture. Such improvements in the characteristics of the kernel can increase the availability of starch for digestion by livestock and in the wet milling process. Thus, the invention provides kernels with increased energy availability for animals, particularly livestock, and kernels which can be used to increase the efficiency of wet milling via increased starch extractability and/or decreased use of chemical reductants.

For clarification, the terms "energy value", "energy availability", "Digestibility" and "Protein Degradability" are defined herein.

The "energy value" of a feed or food, also termed "metabolizable energy (ME) content" is largely determined by energy density (also termed content of "gross energy") and by energy availability. In energy metabolism, the amount of "gross energy" (GE) minus the fecal loss equals "digestible energy" (DE). The amount of "digestible energy" minus the urinary loss equals "metabolizable energy" (ME). The amount of "metabolizable energy" minus heat loss equals "net energy" (NE), which is available to the animal for maintenance and production. See also: Wiseman, J., and Cole, D. J. A. 1985. Energy evaluation of cereals for pig diets. In: Recent Developments in Pig Nutrition. Cole, D. J. A, and Haresign, W. (Eds.), Butterworths, London, pp. 246-262.

"Energy availability" is the degree to which energy-rendering nutrients are available to the animal, often referred to as energy conversion (ratio of metabolizable energy to gross energy or the ratio of net energy to gross energy). Energy availability can be determined with in vivo balance trials, in which excreta are collected by standard methodology (e.g., Sibbald, I. R. 1976. A bioassay for true metabolizable energy in feedstuffs. Poultry Sci. 55:303-308; McNab, J. M., and Blair, J. C. 1988. Modified assay for true and apparent metabolizable energy based upon tube feeding. Br. J. Poultry Sci. 29:697-707; Morgan, D. J., Cole, D. J. A., and Lewis, D. 1975. Energy values in pig nutrition. I. The relationship between digestible energy, metabolizable energy, and total digestible nutrient values of a range of feedstuffs. J.. Agric. Sci. 84:7-17). Energy availability is largely determined by nutrient digestibility in the gastro-intestinal tract, although other factors such as absorption and metabolic utilization also influence energy availability.

"Digestibility" is defined as the fraction of the feed or food that is not excreted as feces. It can be further defined as digestibility of specific components (such as energy or protein) by determining the concentration of these components in the foodstuff and in the excreta. Digestibility can be estimated using in vitro assays, which is routinely done to screen large numbers of different food ingredients and plant varieties. In vitro techniques, including assays with rumen inocula and/or enzymes for ruminant livestock (e.g., Tilley, J. M. A., and Terry, R. A. 1963. A two-stage technique for the in vitro digestion of forage crops. J. Brit. Grassl. Soc. 18:104-111; Pell, A. N., and Schofield, P. 1993. Computerized monitoring of gas production to measure forage digestion in vitro. J. Dairy Sci. 76:1063-1073) and various combinations of enzymes for monogastric animals reviewed in Boisen and Eggum (1991) are also useful techniques for screening transgenic materials for which only limited sample is available. (See Boisen, S., and Eggum, B. O. 1991. Critical Evaluation of in vitro methods for estimating digestibility in simple-stomach animals. Nutr. Res. Rev. 4:141-162).

"Protein Degradability" is defined as the degree to which protein is degraded in a part of the gastrointestinal tract. For example, ruminal protein degradability means the degree to which protein is degraded in the rumen of a ruminant animal. There are a number of assays useful for determining protein degradation, for examples see Mertens, D. R., Rate and Extent of Digestion (pps 13-51), Eds. Forbes, J. N. and France, J. *Quantitative Aspects of Ruminant Digestion and Metabolism*, 1993, CAB International).

Methods for assessing the digestibility and/or energy availability of animal feeds are known in the art. Such methods can be used to determine the digestibility and/or energy availability of the plant parts of the invention, particularly grain. See, for example, Boisen and Fernandez (1997) *Animal Feed Sci. Technol.* 68:277; herein incorporated by reference.

The nucleotide constructs of the invention can also be used to decrease or suppress the expression of endogenous thioredoxin and/or thioredoxin reductases in a plant. Decreasing the expression of enzymes that are involved in the reduction of protein disulfides can limit the reduction of protein disulfides in a plant and can result in an increase in protein disulfides.

The methods of the invention can be used to produce a cereal plant, particularly a maize plant with increased grain hardness. The methods involve increasing the degree of protein disulfide formation during grain fill. Such methods can be used to improve the agronomic properties of, for example, soft-textured maize, particularly opaque-2 or floury-2. Although soft-textured maize such as opaque-2 or floury-2 has a higher feeding value, the agronomic properties are suboptimal. Compared to conventional maize varieties, opaque-2 or floury-2 varieties generally display reduced disease resistance and increased grain breakage during handling. By reducing or eliminating the level and/or activity of TRX or NTR in maize kernels, the excessively soft kernels of opaque-2 or floury-2 genotypes can be ameliorated. Thus, the methods of the invention find use in increasing the hardness of soft-textured grain by increasing the degree of protein disulfides formed during grain fill.

Similarly, the methods of the invention can be used to increase the hardness of maize kernels to produce kernels with reduced energy availability and digestibility. Such kernels will have a reduced effective caloric content when digested by animals, and thus find use in the production of diet foods for humans and pets.

The methods of the invention for increasing grain hardness of a plant involve reducing or suppressing the level or activity of at least one protein involved in disulfide bond reduction in a plant seed, preferably during seed development or grain fill. Preferred proteins are thioredoxin h's and thioredoxin reductases, particularly those thioredoxin h's and thioredoxin reductases which occur in seed and grain. The plant can be transformed with the TRX or NTR nucleotide sequences in the sense orientation for co-suppression or sense suppression of gene expression. Alternatively, the plant can be transformed with the TRX or NTR nucleotide sequences in the antisense orientation for antisense suppression. Disulfide formation can also be suppressed by modifying genomic sequences in plant by chimeraplasty. Generally, such modifications will alter the amino acid sequence of the proteins encoded by the genomic sequence as to reduce or eliminate the activity of a TRX or NTR in a plant, particularly in a seed, more particularly in a developing seed.

Compositions of the invention include nucleotide sequences encoding TRX and NTR proteins that are involved in regulating the disulfide status of proteins. In particular, the present invention provides for isolated nucleic acid molecules comprising nucleotide sequences encoding the amino acid sequences shown in SEQ ID NOs:2, 4, 6, 8, 10, 12, 14, 16, 19, 21, 23, and 25 or the nucleotide sequences encoding the DNA sequences deposited in a bacterial host as Patent Deposit Nos. PTA-2428. Further provided are polypeptides having an amino acid sequence encoded by a nucleic acid molecule described herein, for example those set forth in SEQ ID NOs: 1, 3, 5, 7, 9, 11, 13, 15, 17, 18, 20, 22 and 24, those deposited in a bacterial host as Patent Deposit No. PTA-2428, and fragments and variants thereof.

Plasmids containing the nucleotide sequences of the invention, particularly SEQ ID NOs: 5, 7, 9, 11, 13, 20, 22 and 24, were deposited on Aug. 29, 2000 with the Patent Depository of the American Type Culture Collection (ATCC), Manassas, Va., and assigned Patent Deposit Nos. PTA-2428. The deposit will be maintained under the terms of the Budapest Treaty on the International Recognition of the Deposit of Microorganisms for the Purposes of Patent Procedure. The deposit was made merely as a convenience for those of skill in the art and are not an admission that a deposit is required under 35 U.S.C. §112.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence TRX or NTR activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a TRX nucleotide sequence that encodes a biologically active portion of a TRX protein of the invention will encode at least 15, 25, 30, 50, 75, 100, or 125 contiguous amino acids, or up to the total number of amino acids present in a full-length TRX protein of the invention (for example, 128, 128, 63, 134, 123, 122, 126, 122, and 122 amino acids for SEQ ID NO:2, 4, 6, 8, 10, 12, 14, 16, and 19, respectively). Fragments of a TRX nucleotide sequence that are useful as hybridization probes or PCR primers generally need not encode a biologically active portion of a TRX protein.

Thus, a fragment of a TRX nucleotide sequence may encode a biologically active portion of a TRX protein, or it may be a fragment that can be used as a hybridization probe or PCR primer using methods disclosed below. A biologically active portion of a TRX protein can be prepared by isolating a portion of one of the TRX nucleotide sequences of the invention, expressing the encoded portion of the TRX protein (e.g., by recombinant expression in vitro) and assessing the activity of the encoded portion of the TRX protein. Nucleic acid molecules that are fragments of an TRX nucleotide sequence comprise at least 16, 20, 50, 75, 100, 150, 200, 250, 300, 350, 400, 450, 500, 550, 600, 650, or 700 nucleotides, or up to the number of nucleotides present in a full-length TRX nucleotide sequence disclosed herein (for example, 797, 799, 367, 720, 722, 727, 700, 658, 580, and 590 nucleotides for SEQ ID NOs:1, 3, 5, 7, 9, 11, 13, 15, 17, and 18, respectively).

A fragment of an NTR nucleotide sequence that encodes a biologically active portion of an NTR protein of the invention will encode at least 15, 25, 30, 50, 100, 150, 200, 250, or 300 contiguous amino acids, or up to the total number of amino acids present in a full-length NTR protein of the invention (for example, 244, 111, and 331 amino acids for SEQ ID NOs:21, 23, and 25, respectively). Fragments of an NTR nucleotide sequence that are useful as hybridization probes or PCR primers generally need not encode a biologically active portion of an NTR protein.

Thus, a fragment of an NTR nucleotide sequence may encode a biologically active portion of an NTR protein, or it may be a fragment that can be used as a hybridization probe or PCR primer using methods disclosed below. A biologically active portion of an NTR protein can be prepared by isolating a portion of one of the NTR nucleotide sequences of the invention, expressing the encoded portion of the NTR protein (e.g., by recombinant expression in vitro), and assessing the activity of the encoded portion of the NTR protein. Nucleic acid molecules that are fragments of an NTR nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, or 1,400 nucleotides, or up to the number of nucleotides present in a full-length NTR nucleotide sequence disclosed herein (for example, 948, 556, and 1336 nucleotides for SEQ ID NOs:20, 22, and 24, respectively).

By "variants" is intended substantially similar sequences. For nucleotide sequences, conservative variants include those sequences that, because of the degeneracy of the genetic code, encode the amino acid sequence of one of the TRX or NTR polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a TRX or NTR protein of the invention. Generally, variants of a particular nucleotide sequence of the invention will have at least about 80% generally at least about 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, TRX or NTR activity as described herein. Such variants may result from, for example, genetic polymorphism or from human manipulation. Biologically active variants of a native TRX or NTR protein of the invention will have at least about 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the TRX or NTR proteins can be prepared by mutations in the DNA. Methods for mutagenesis and nucleotide sequence alterations are well known in the art. See, for example, Kunkel (1985) *Proc. Natl. Acad. Sci.*USA 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired TRX or NTR activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assays for TRX activity or NTR activity. See, for example, Jacquot et al. (1995) *Meth. Enzymol.* 252: 240-252, Gautier et al. (1998) *Eur. J. Biochem.* 252:314-324 and Holmgren (1979) *J. Biol. Chem.* 254:9627-9632, herein incorporated by reference.

Variant nucleotide sequences and proteins also encompass sequences and proteins derived from a mutagenic and recombinogenic procedure such as DNA shuffling. With such a procedure, one or more different TRX coding sequences can be manipulated to create a new TRX protein possessing the desired properties. Similarly, one or more NTR sequences can be manipulated to create a new NTR protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the TRX gene of the invention and other known TRX genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire TRX or NTR nucleotide sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the TRX or NTR sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire TRX or NTR sequence disclosed herein, or one or more portions thereof, may be used as a probe capable of specifically hybridizing to corresponding TRX or NTR sequences and messenger RNAs. To achieve specific hybridization under a variety of conditions, such probes include sequences that are unique among TRX or NTR sequences and are preferably at least about 10 nucleotides in length, and most preferably at least about 20 nucleotides in length. Such probes may be used to amplify corresponding TRX or NTR sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2× SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.$+16.6$ (log M)$+0.41$ (% GC)$-0.61$ (% form) $-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Isolated sequences that encode for a TRX protein and which hybridize under stringent conditions to the TRX sequences disclosed herein, or to fragments thereof, are encompassed by the present invention. Isolated sequences that encode for an NTR protein and which hybridize under stringent conditions to the NTR sequences disclosed herein, or to fragments thereof, are encompassed by the present invention.

The following terms are used to describe the sequence relationships between two or more nucleic acids or polynucleotides:(a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. Alignment may also be performed manually by inspection.

Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

For purposes of the present invention, comparison of nucleotide or protein sequences for determination of percent sequence identity to the TRX and NTR sequences disclosed herein is preferably made using CLUSTAL with the following changes from the default parameters. For amino acid sequence comparisons a Gap Penalty of 10 and Gap Length Penalty of 10 was used for multiple alignments and a KTUPLE of 2, Gap Penalty of 3, Window of 5 and Diagonals Saved of 5 was used for pairwise alignments. For nucleotide sequence comparisons, a Gap Penalty of 10 and Gap Length Penalty of 10 was used for multiple alignments and a KTUPLE of 2, Gap Penalty of 5, Window of 4 and Diagonals Saved of 4 was used for pairwise alignments. Any equivalent program can also be used to determine percent sequence identity. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an anti-sense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al (1999) *Proc. Natl. Acad. Sci. USA* 96:8774-8778; herein incorporated by reference.

The TRX and NTR sequences of the invention are provided in expression cassettes for expression in the plant of interest. The cassette will include 5' and 3' regulatory sequences operably linked to a TRX or NTR nucleotide sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the TRX or NTR nucleotide sequence to be under the transcriptional regulation of the regulatory regions. The expression cassette may additionally contain selectable marker genes.

The expression cassette will include in the 5'-3' direction of transcription, a transcriptional and translational initiation region, a TRX or NTR DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of TRX or NTR in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immuno-globulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, chemically regulated, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Chemically regulated promoters can be used to modulate the expression of a gene in a plant through the application of an exogenous chemical regulator. Depending upon the objective, the promoter may be a chemical inducible promoter, where application of the chemical induces gene expression, or a chemical repressible promoter, where application of the chemical represses gene expression. Chemical inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemically regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced TRX or NTR expression within a particular plant tissue. Tissue-preferred promoters include Yamamoto et al. (1997) *Plant J.* 12(2)255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2):

513-524; Yamamoto et al. (1994) *Plant Cell Physiol.* 35(5): 773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-specific promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-specific promoters are known and can be selected from the many available from the literature or isolated de novo from various compatible species. See, for example, Hire et al. (1992) *Plant Mol. Biol.* 20(2): 207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1): 11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed ro1C and ro1D root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and ro1B promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see WO 00/11177, herein incorporated by reference). The 27 kDa gamma-zein promoter is a preferred endosperm-specific promoter. The maize globulin-1 and oleosin promoters are preferred embryo-specific promoters. For dicots, seed-specific promoters include, but are not limited to, bean β-phaseolin, napin, β-conglycinin, soybean lectin, cruciferin, and the like. For monocots, seed-specific promoters include, but are not limited to, promoters of the 15 kDa beta-zein, 22 kDa alpha-zein, 27 kDa gamma-zein, waxy, shrunken 1, shrunken 2, globulin 1 and oleosin genes. See also WO 00/12733, where seed-preferred promoters from end1 and end2 genes are disclosed; herein incorporated by reference.

In a preferred embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts or other plastids. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The TRX and NTR proteins of the invention can be targeted to specific compartments within the plant cell. Methods for targeting proteins to a specific compartment are known in the art. Generally, such methods involve modifying the nucleotide sequence encoding the protein in such a manner as to add or remove specific amino acids from the protein encoded thereby. Such amino acids comprise targeting signals for targeting the protein to a specific compartment such as, for example, a the plastid, the nucleus, the endoplasmic reticulum, the vacuole, the mitochondrion, the peroxisome, the Golgi apparatus, and for secretion from the cell. Targeting sequences for targeting a protein to a specific cellular compartment, or for secretion, are known to those of ordinary skill in the art. Chloroplast-targeting or plastid-targeting sequences are known in the art and include the chloroplast small subunit of ribulose-1,5-bisphosphate carboxylase (Rubisco) (de Castro Silva Filho et al. (1996) *Plant Mol. Biol.* 30:769-780; Schnell et al. (1991) *J. Biol. Chem.* 266(5):3335-3342); 5-(enolpyruvyl)shikimate-3-phosphate synthase (EPSPS) (Archer et al. (1990) *J. Bioenerg. Biomemb.* 22(6): 789-810); tryptophan synthase (Zhao et al. (1995) *J. Biol. Chem.* 270(11):6081-6087); plastocyanin (Lawrence et al. (1997) *J. Biol. Chem.* 272(33):20357-20363); chorismate synthase (Schmidt et al. (1993) *J. Biol. Chem.* 268(36): 27447-27457); and the light harvesting chlorophyll a/b binding protein (LHBP) (Lamppa et al. (1988) *J. Biol. Chem.* 263:14996-14999). See also Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566;

Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

The invention involves transforming host cells with the nucleotide constructs of the invention. Generally, the nucleotide construct will comprise a TRX or NTR nucleotide sequence of the invention operably linked to a promoter that drives expression in the host cell of interest. Host cells include, but are not limited to: plant cells; animal cells; fungal cells, particularly yeast cells; and bacterial cells.

The methods of the invention involve introducing a nucleotide construct into a plant. By "introducing" is intended presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Bio-technology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The nucleotide constructs of the invention may also be introduced into plants by contacting plants with a virus or viral nucleic acids. Generally, such methods involve incorporating a nucleotide construct of the invention within a viral DNA or RNA molecule. It is recognized that the an TRX or NTR of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The present invention may be used for transformation of any plant species, including, but not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, *Brassica*, soybean, cotton, safflower, peanut, sorghum, wheat, barley, rice, sorghum, rye, millet, tobacco, etc.), more preferably cereal plants, yet more preferably corn, wheat, barley, rice, sorghum, rye and millet plants.

It is recognized that with these nucleotide sequences, antisense constructions, complementary to at least a portion of the messenger RNA (mRNA) for a TRX or NTR sequence can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a nucleotide construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The following examples are presented by way of illustration, not by way of limitation.

EXPERIMENTAL

Example 1

Transformation and Regeneration of Maize With TRX and/or NTR Nucleotide Constructs Immature maize embryos from greenhouse donor plants are bombarded with a plasmid containing a TRX and/or NTR nucleotide sequence operably linked to the promoter of the 19 KD α-zein gene and the 70 KD heat-shock gene plus a plasmid containing the selectable marker gene PAT (Wohlleben et al. (1988) *Gene* 70:25-37) that confers resistance to the herbicide Bialaphos. Transformation is performed as follows. Media recipes follow below.

Preparation of Target Tissue

The ears are surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising a TRX and/or NTR nucleotide sequence operably linked to the promoter of the 19 KD α-zein gene and the 70 KD heat-shock gene is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in TrisEDTA buffer (1 μg total)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Seeds are monitored and scored for TRX or NTR protein or activity levels.

Bombardment and Culture Media

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1 511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.1 0 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 2

Agrobacterium-Mediated Transformation of Maize with TRX and/or NTR Nucleotide Constructs For *Agrobacterium*-mediated transformation of maize with a TRX and/or NTR nucleotide sequence, preferably the method of Zhao is employed (PCT patent publication WO98/32326), the contents of which are hereby incorporated by reference. Briefly, immature embryos are isolated from maize and the embryos contacted with a suspension of Agrobacterium, where the bacteria are capable of transferring the TRX or NTR nucleotide sequence, to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

Maize plants were transformed with nucleotide constructs comprising TRX, NTR, or both, by the Agrobacterium-mediated transformation method of Zhao essentially as described above. The constructs additionally comprised the 27 kDa gamma-zein promoter operably linked to each of the TRX or NTR nucleotide sequences to drive expression in seeds. The constructs used are listed in Table 1. The TRX nucleotide sequence is from SEQ ID NO: 13 and the NTR nucleotide sequence is from SEQ ID NO: 24.

Constructs 1, 2, and 4 find use in the overexpression of the respective TRX and NTR nucleotide sequences in maize seeds to improve the digestibility, energy availability and wet milling properties of the grain. Construct 3 finds use reducing NTR levels in the seed by co-suppression, and thus resulting in an increase in the hardness of the endosperm of the maize kernel. The truncated NTR nucleotide sequence in Construct 3 corresponds of nucleotides 1 to 744 SEQ ID NO:24.

TABLE 1

Nucleotide Constructs for Maize Transformation

| Construct | Promoter | Expressed Sequence |
| --- | --- | --- |
| 1 | Gamma zein | TRX |
| 2 | Gamma zein | NTR |
| 3 | Gamma zein | NTRtr* |

TABLE 1-continued

Nucleotide Constructs for Maize Transformation

| Construct | Promoter | Expressed Sequence |
|---|---|---|
| 4 | Gamma zein | TRX |
|   | Gamma zein | NTR |

*Truncated NTR sequence

Example 3

Reduction of Disulfide Bonds in Different Forms of Grain Improves Digestibility

Ground corn was pretreated by overnight soak in a strong reducing agent, 1 mM DTT (ditiothreietol) versus a control solution without DTT. Enzyme digestible dry matter percent (EDDM %) of the grain was measured using the method of Boisen and Fernandez (1997) *Animal Feed Sci. Technol.* 68:277. As can be seen in FIG. 1, pretreatment in DTT improves in vitro dry matter digestibility of mature grain sampled at black layer by about 12% units. Digestibility of immature grain, sampled at late dough/silage maturity, is equally improved by pretreatment with DTT. As overexpression of thioredoxin h and/or NTR promotes protein disulfide reduction, these data indicate that both mature grain and immature grain will benefit from reduced protein disulfide cross-links as a result of overexpression of thioredoxin h and/or NTR. Improvements in digestibility of immature grain through the methods of this invention can be extrapolated to concomitant improvements in digestibility of silage, about half of which consists of immature grain similar to the kernels tested at late dough stage.

Example 4

Detection of NTR and TRX in Maize Kernels

Transformed maize plants were prepared as described in Example 2. The plants were self pollinated ears containing the kernels ($T_2$) were harvested. These $T_2$ kernels were sown, allowed to grow into plants, and then self pollinated. The resulting $T_3$ kernels were analyzed for the expression of NTR, TRX, or both, via Western dot blot analyses as described below.

Protein extraction: One whole endosperm (immature or mature) or endosperm chip was harvested from each kernel, ground and placed into labeled mega titer plates. Two-hundred microliters of 1× SDS protein extraction buffer were added to each megatiter tube and boiled for 3 minutes on a dri bath at 100° C. [SDS Protein Extraction Buffer (2×): Combine 40 mL 20% aqueous SDS solution, 40 mL 0.5M Tris pH 6.8 and 120 mL deionized, distilled sterile water. Dilute to 1× and add Dithiotreitol (DTT) to 10 mM immediately before use.] After boiling, the samples were returned to the mega titer plate in their correct positions and were centrifuged at 3000 rpm for 20 minutes. The supernatant of each sample was then collected and placed in fresh tubes in a new mega titer plate, retaining plate position.

Dot blot analysis: Nitrocellulose membranes (0.45 μm) were prepared for each set of 96 samples by cutting to size and appropriate labeling. Three microliters of each sample were blotted onto the appropriate membrane using an 8 channel pipettor. After all 96 blots were made to each membrane, the membrane was allowed to dry for approximately 5 minutes. Then, each dry membrane was placed into deionized, distilled sterile water until the membrane was fully wetted (determined by disappearance of sample dots). Each fully wetted membrane was then placed into approximately 30 mL of 3% milk solution and gently agitated for 10 minutes on a platform shaker. [3% Milk Solution: Dissolve 15 g of nonfat dry milk in 250 mL TBST buffer (see below).] Following this blocking period, the milk was discarded and replaced by a 1:1000 solution of Thioredoxin Reductase primary antibody and/or Thrioredoxin h primary antibody in 3% milk solution for overnight incubation. Incubation occurred at 4° F. with gentle agitation on a platform shaker in a covered container. The primary antibody solution was removed the next morning. The membrane was then washed 3 times with plain 3% milk solution for 15 minutes each wash. After the final wash, the milk solution was replaced with a 1:5000 solution of horseradish peroxidase conjugate secondary antibody in 3% milk solution and incubated at room temperature with gentle agitation for 1 hour. The secondary antibody solution was then discarded and the membrane washed 2 times with plain 3% milk solution for 15 minutes each wash and then with plain TBST buffer (30 mL 1 M Tris solution with 5.84 g NaCl and 0.75 mL Tween 20 surfactant and 1470 mL deionized, distilled sterile water) for 15 minutes.

Membranes were then placed in pre-cut heat sealed pouches for development. A 1 mL aliquot of pre-mixed ECL Western blotting solution was pipetted onto the protein side of each membrane and then heat sealed to prevent leakage during development. Membranes were allowed to incubate in the detection solution for 1 minute and then placed on film in the dark room for detection, with an exposure time of 15 seconds.

Example 5

Overexpression of NTR in Immature Maize Kernels

NTR expression in immature endosperm from maize plants transformed with Construct 2 (see Example 2) was determined. Immature endosperm was isolated from individual maize kernels ($T_3$) harvested at 22 days after pollination. NTR protein levels were analyzed as described in Example 4. NTR protein was not detected in immature endosperm from non-transformed control plants. The results of the analyses are indicated in Table 2. The results indicate that the transformed plants overexpressed NTR in immature endosperm. The results also indicate that not all of the $T_2$ plants are homozygous for the NTR transgene.

TABLE 2

Overexpression of NTR in the Immature Endosperm of Individual Maize Kernels ($T_3$) Harvested From $T_2$ Plants

| $T_2$ Plant | No. of Kernels ($T_3$) Overexpressing NTR in Immature Endosperm | Total No. of Kernels Assayed |
|---|---|---|
| R2 | 7 | 8 |
| R3 | 8 | 8 |
| R4 | 8 | 8 |
| R5 | 6 | 8 |
| R5 | 7 | 8 |
| R6 | 8 | 8 |
| R7 | 7 | 8 |
| R8 | 7 | 8 |
| R9 | 8 | 8 |

Example 6

Overexpression of TRX in Immature Maize Kernels

TRX expression in immature endosperm from maize plants transformed with Construct 1 (see Example 2) was determined. Immature endosperm was isolated from individual maize kernels ($T_3$) harvested at 22 days after pollination. TRX protein levels were analyzed as described in Example 4. TRX protein was not detected in immature endosperm from non-transformed control plants. The results of the analyses are indicated in Table 3. The results indicate that the transformed plants overexpressed TRX in immature endosperm. The results also indicate that not all of the $T_2$ plants are homozygous for the TRX transgene.

TABLE 3

Overexpression of TRX in the Immature Endosperm of Individual Maize Kernels ($T_3$) Harvested From $T_2$ Plants

| $T_2$ Plant | No. of Kernels ($T_3$) Overexpressing TRX in Immature Endosperm | Total No. of Kernels Assayed |
| --- | --- | --- |
| X1 | 8 | 8 |
| X2 | 7 | 8 |
| X3 | 5 | 8 |
| X4 | 4 | 8 |
| X5 | 8 | 8 |
| X6 | 8 | 8 |
| X7 | 7 | 8 |
| X8 | 5 | 8 |
| X9 | 3 | 8 |

Example 7

Overexpression of NTR/TRX in Immature Maize Kernels

NTR and TRX expression in immature endosperm from maize plants transformed with Construct 4 (see Example 2) was determined. Immature endosperm was isolated from individual maize kernels ($T_3$) harvested at 22 days after pollination. NTR and TRX protein levels were analyzed as described in Example 4. NTR and TRX protein was not detected in immature endosperm from non-transformed control plants. The results of the analyses are indicated in Table 4. The results indicate that the transformed plants overexpressed NTR and TRX in immature endosperm. The results also indicate that not all of the $T_2$ plants are homozygous for the NTR and TRX transgenes.

TABLE 4

Overexpression of NTR and TRX in the Immature Endosperm of Individual Maize Kernels ($T_3$) Harvested From $T_2$ Plants

| $T_2$ Plant | No. of Kernels ($T_3$) Overexpressing NTR and TRX in Immature Endosperm | Total No. of Kernels Assayed |
| --- | --- | --- |
| RX1 | 7 | 8 |
| RX3 | 8 | 8 |
| RX4 | 4 | 8 |
| RX5 | 5 | 8 |
| RX6 | 8 | 8 |
| RX7 | 5 | 8 |
| RX8 | 8 | 8 |
| RX10 | 8 | 8 |
| RX11 | 7 | 8 |
| RX14 | 8 | 8 |
| RX15 | 8 | 8 |
| RX16 | 8 | 8 |
| RX16 | 8 | 8 |
| RX19 | 8 | 8 |
| RX20 | 4 | 8 |
| RX21 | 5 | 8 |

Example 8

Overexpression of NTR in Mature Maize Kernels

NTR expression in mature endosperm from maize plants transformed with Construct 2 (see Example 2) was determined. Mature endosperm was isolated from individual maize kernels ($T_3$). NTR protein levels were analyzed as described in Example 4. NTR protein was not detected in mature endosperm from non-transformed control plants. The results of the analyses are indicated in Table 5. The results indicate that the transformed plants overexpressed NTR in mature endosperm. The results also indicate that not all of the $T_2$ plants are homozygous for the NTR transgene.

TABLE 5

Overexpression of NTR in the Endosperm of Individual Mature Maize Kernels ($T_3$) Harvested From $T_2$ Plants

| $T_2$ Plant | No. of Kernels ($T_3$) Overexpressing NTR in Endosperm | Total No. of Kernels Assayed |
| --- | --- | --- |
| R2 | 6 | 8 |
| R3 | 6 | 8 |
| R4 | 4 | 8 |
| R5 | 3 | 8 |
| R6 | 8 | 8 |
| R7 | 7 | 8 |
| R8 | 7 | 8 |
| R9 | 6 | 8 |

Example 9

Overexpression of TRX in Mature Maize Kernels

TRX expression in mature endosperm from maize plants transformed with Construct 1 (see Example 2) was determined. Mature endosperm was isolated from individual maize kernels ($T_3$). TRX protein levels were analyzed as described in Example 4. TRX protein was not detected in mature endosperm from non-transformed control plants. The results of the analyses are indicated in Table 6. The results indicate that the transformed plants overexpressed TRX in mature endosperm. The results also indicate that not all of the $T_2$ plants are homozygous for the TRX transgene.

TABLE 6

Overexpression of TRX in the Endosperm of Individual Mature Maize Kernels ($T_3$) Harvested From $T_2$ Plants

| $T_2$ Plant | No. of Kernels ($T_3$) Overexpressing TRX in Endosperm | Total No. of Kernels Assayed |
|---|---|---|
| X2 (ear 1) | 7 | 8 |
| X2 (ear 2) | 2 | 8 |
| X2 (ear 3) | 4 | 8 |

Example 10

Overexpression of NTR/TRX in Mature Maize Kernels

NTR and TRX expression in mature endosperm from maize plants transformed with Construct 4 (see Example 2) was determined. Mature endosperm was isolated from individual maize kernels ($T_3$). NTR and TRX protein levels were analyzed as described in Example 4. NTR and TRX proteins were not detected in mature endosperm from non-transformed control plants. The results of the analyses are indicated in Table 7. The results indicate that the transformed plants overexpressed NTR and TRX in mature endosperm. The results also indicate that not all of the $T_2$ plants are homozygous for the NTR transgene.

TABLE 7

Overexpression of NTR and TRX in the Endosperm of Individual Mature Maize Kernels ($T_3$) Harvested From $T_2$ Plants

| $T_2$ Plant | No. of Kernels ($T_3$) Overexpressing NTR and TRX in Endosperm | Total No. of Kernels Assayed |
|---|---|---|
| RX1 | 6 | 8 |
| RX3 | 8 | 8 |
| RX5 | 5 | 8 |
| RX6 | 8 | 8 |
| RX8 | 7 | 8 |
| RX10 | 8 | 8 |
| RX14 | 8 | 8 |
| RX16 | 8 | 8 |
| RX20 | 8 | 8 |

Example 11

Mature Maize Kernels Overexpressing TRX and NTR Have Improved Digestibility

Enzyme digestible dry matter percent (EDDM%) of the grain was determined as described in Example 3. $T_3$ maize kernels overexpressing NTR, TRX, and both NTR and TRX were analyzed for digestibility as determined by EDDM%. The transformed plants were prepared as described in Example 2. Kernels from wild-type segregants of the transformed plants were used as controls. The results of the digestibility analyses are provided in Tables 8-11.

With kernels from the wild-type segregants (Table 8), digestibility was significantly increased (p=0.001) in wild-type kernels when there was a DTT pretreatment prior to digestion. These results are similar to those described in Example 3.

TABLE 8

Digestibility (4h-EDDM (%)) of Kernels of Wild-Type Segregants from Maize Plants Transformed with NTR, TRX, NTR/TRX

| Event | −DTT | SD | +DTT | SD | Diff.* |
|---|---|---|---|---|---|
| RX1-WT | 62.7 | 2.3 | 67.0 | 3.5 | 4.3 |
| RX8-WT | 62.1 | 3.4 | 65.0 | 2.0 | 2.8 |
| RX10-WT | 61.4 | 1.4 | 65.3 | 1.5 | 3.8 |
| RX9-WT | 63.6 | 2.0 | 67.8 | 1.7 | 4.1 |
| R2-WT | 61.7 | 1.0 | 67.8 | 2.7 | 6.1 |
| R3-WT | 61.7 | 1.1 | 69.2 | 4.2 | 7.4 |
| X2-WT | 57.8 | 4.0 | 68.9 | 3.7 | 11.1 |
| X2-WT | 60.5 | 3.0 | 73.1 | 3.7 | 12.6 |
| AVG | 61.5 | 1.7 | 68.0 | 2.6 | 6.5 |

*t-test for difference between +/−DTT, p = 0.001.

When kernels were overexpressing NTR (Table 9), the digestibility of the kernels in the absence a DTT pretreatment was significantly increased (p=0.000) over the digestibility of kernels from the wild-type segregants. This result indicates that expression of NTR in maize kernels can increase the digestibility of the kernels as evidenced by an increase in EDDM %. The DTT pretreatment further increased the digestibility of the NTR overexpressing kernels.

TABLE 9

Digestibility (4h-EDDM (%)) of Maize Kernels Overexpressing NTR

| Event | −DTT | SD | +DTT | SD | Diff.* |
|---|---|---|---|---|---|
| R1 | 64.8 | 1.4 | 64.2 | 2.8 | −0.6 |
| R1 | 65.2 | 1.9 | 70.2 | 2.9 | 4.9 |
| R3 | 67.3 | 2.0 | 68.8 | 2.8 | 1.4 |
| R4 | 67.6 | 1.6 | 73.1 | 2.9 | 5.5 |
| R6 | 66.3 | 2.5 | 69.3 | 2.4 | 3.0 |
| R6 | 72.3 | 0.3 | 69.4 | 0.9 | −2.9 |
| R7 | 63.8 | 3.3 | 67.1 | 2.9 | 3.3 |
| R7 | 64.5 | 4.1 | 66.2 | 0.3 | 1.8 |
| R8 | 68.6 | 4.7 | 74.1 | 1.1 | 5.4 |
| R8 | 65.2 | 3.5 | 67.0 | 1.3 | 1.7 |
| R9 | 66.2 | 1.8 | 67.9 | 3.9 | 1.7 |
| AVG | 66.5 | 2.4 | 68.8 | 2.9 | 2.3 |

*t-test for difference between +/−DTT, p = 0.007.
t-test for difference between −DTT in Table 9 (NTR) and −DTT (WT) in Table 8, p = 0.000.

In Table 10, the digestibility results from kernels overexpressing TRX are provided. In the absence of DTT, the digestibility of the kernels was not significantly different from the digestibility of kernels from wild-type segregants. While the results in Table 10 do not show that overexpression of TRX alone increased digestibility, it is possible that the TRX expression might not have been high enough to affect digestibility in the EDDM assay. Thus, further increasing the expression of TRX by, for example, using a stronger promoter to drive the expression of the TRX nucleotide sequence in the kernels, may lead to an increase in digestibility.

TABLE 10

Digestibility (4h-EDDM (%)) of Maize Kernels Overexpressing TRX

| Event | −DTT | SD | +DTT | SD | Diff.* |
|---|---|---|---|---|---|
| X1 | 62.0 | 2.8 | 69.1 | 3.6 | 7.1 |
| X1 | 63.0 | 3.2 | 70.7 | 1.0 | 7.7 |
| X1 | 62.4 | 2.5 | 73.5 | 2.5 | 11.1 |
| X1 | 59.5 | 2.7 | 74.3 | 3.0 | 14.8 |
| X2 | 58.6 | 2.3 | 67.6 | 5.1 | 9.0 |
| X2 | 62.5 | 2.3 | 69.0 | 3.4 | 6.6 |

TABLE 10-continued

Digestibility (4h-EDDM (%)) of Maize Kernels Overexpressing TRX

| Event | −DTT | SD | +DTT | SD | Diff.* |
|---|---|---|---|---|---|
| X2 | 61.5 | 1.2 | 62.5 | 2.3 | 1.0 |
| AVG | 61.3 | 1.7 | 69.5 | 3.9 | 8.2 |

*t-test for difference between +/−DTT, p = 0.001.
t-test for difference between −DTT in Table 10 (TRX) and −DTT (WT) in Table 8, p = 0.440.

The digestibility of kernels overexpressing both NTR and TRX was determined (Table 11). Similar to the digestibility of kernels overexpressing NTR, the digestiblity of NTR/TRX overexpressing kernels was significantly increased (p=0.000) above the digestibility of kernels from the wild-type segregants. Furthermore, the digestibility of the NTR/TRX overexpressing kernels was significantly increased (p=0.087) over the digestibility of the NTR overexpressing kernels. These results indicate that the digestibility of kernels overexpressing NTR, and kernels overexpressing both NTR and TRX, is increased significantly, when compared to the digestibility of kernels from wild-type plants.

TABLE 11

Digestibility (4h-EDDM (%)) of Maize Kernels Overexpressing Both NTR and TRX

| Event | −DTT | SD | +DTT | SD | Diff.* |
|---|---|---|---|---|---|
| RX3 | 68.0 | 1.0 | 71.0 | 0.6 | 3.0 |
| RX5 | 68.5 | 1.6 | 71.0 | 1.6 | 2.5 |
| RX8 | 68.0 | 1.7 | 65.7 | 3.2 | −2.3 |
| RX10 | 65.3 | 3.2 | 71.8 | 2.1 | 6.6 |
| RX14 | 65.0 | 1.6 | 71.5 | 2.0 | 6.5 |
| RX15 | 72.3 | 2.3 | 75.7 | 1.3 | 3.4 |
| RX15 | 67.6 | 2.7 | 70.6 | 1.1 | 3.0 |
| RX15 | 73.6 | 2.5 | 73.9 | 2.0 | 0.4 |
| RX16 | 69.9 | 0.8 | 72.3 | 0.8 | 2.4 |
| RX17 | 64.1 | 0.6 | 66.5 | 0.7 | 2.4 |
| AVG | 68.2 | 3.1 | 71.0 | 3.0 | 2.8 |

*t-test for difference between +/−DTT, p = 0.004.
t-test for difference between −DTT in Table 11 (NTR/TRX) and −DTT (WT) in Table 8, p = 0.000.
t-test for difference between −DTT in Table 11 (NTR/TRX) and −DTT (NTR) in Table 9, p = 0.087.

The results disclosed herein demonstrate that the methods of the invention can be used to produce corn kernels with improved digestibility. Additionally, Examples 5-7 indicated that NTR and TRX can be overexpressed in immature endosperm. Therefore, similar improvements on the digestibility of immature kernels overexpressing NTR and and NTR/TRX are also expected. Finally, improvements in the digestibility of immature grain through the methods of this invention can be extrapolated to concomitant improvements in digestibility of silage, about half of which consists of immature grain similar to the kernels tested at late dough stage (FIG. 1).

Example 12

Figure 2:
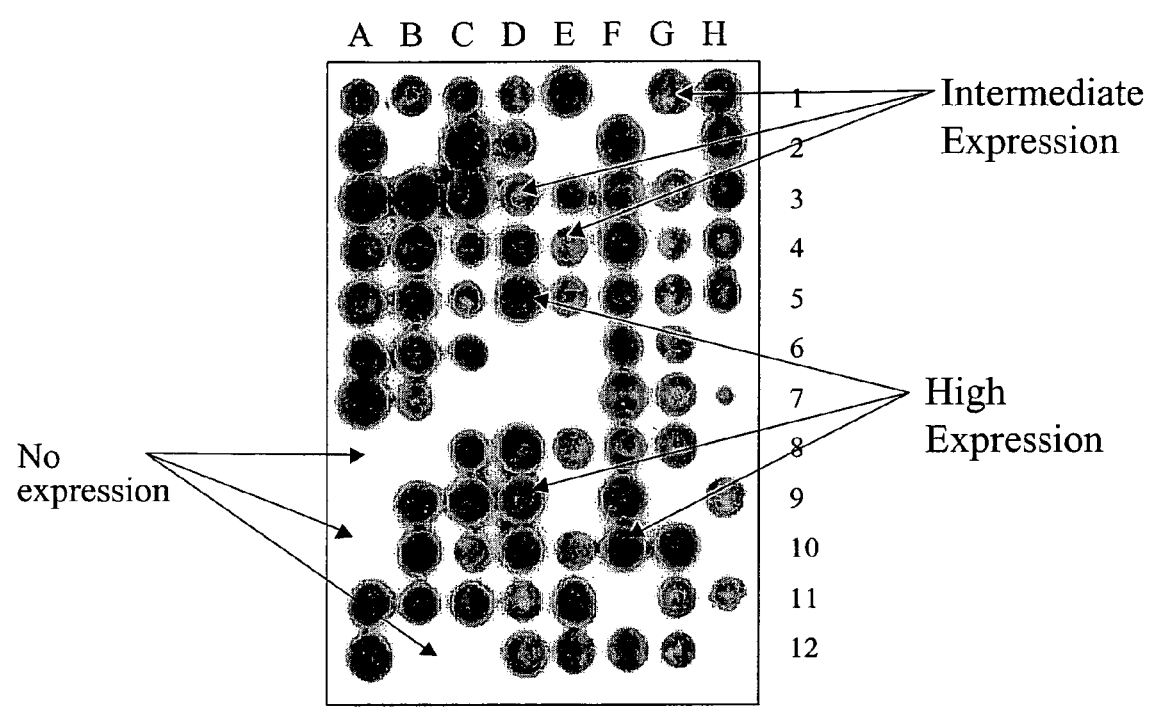
FIG. 2 is a photographic representation of the results of a Western dot blot analysis to assess the expression levels of NTR protein in the mature endosperm of individual $T_3$ maize kernels. The kernels were harvested from a single $T_2$ plant transformed with the an NTR nucleotide sequence of the invention operable linked to the gamma zein promoter (Construct 2) as described in Example 2.

Digestibility of Mature Maize Kernels is Correlated with NTR Expression in the Kernels The results provided in Example 11 indicate that the overexpression of NTR and NTR/TRX in grain increases the digestibility of grain. To verify that the expression level of NTR in mature endosperm is correlated with digestibility of kernels, endosperm chips were isolated from $T_3$ maize kernels harvested from a single $T_2$ NTR transformation event (R3). The NTR protein level in each endosperm chip was determined using the Western dot blot method described in Example 4. The results of a typical dot blot analysis are depicted in FIG. 2. Individual kernels were then designated as no expression, intermediate expression, and high expression of NTR protein based on the Western dot blot results with the endosperm chips. The remaining portions of the no expression, intermediate expression, and high expression kernels were grouped according to expression levels. Each group of kernels was then analyzed separately for digestibility as described in Example 3. The results of those analyses are graphically depicted in FIG. 3. In the absence of DTT, the no NTR expression kernels displayed the lowest level of digestibility, the intermediate NTR expression kernels displayed an intermediate level of digestibility, and the high NTR expression kernels displayed the highest level of digestibility. The results demonstrate that the level of NTR protein in the endosperm is positively correlated with the digestibility of the kernel.

Figure 3:
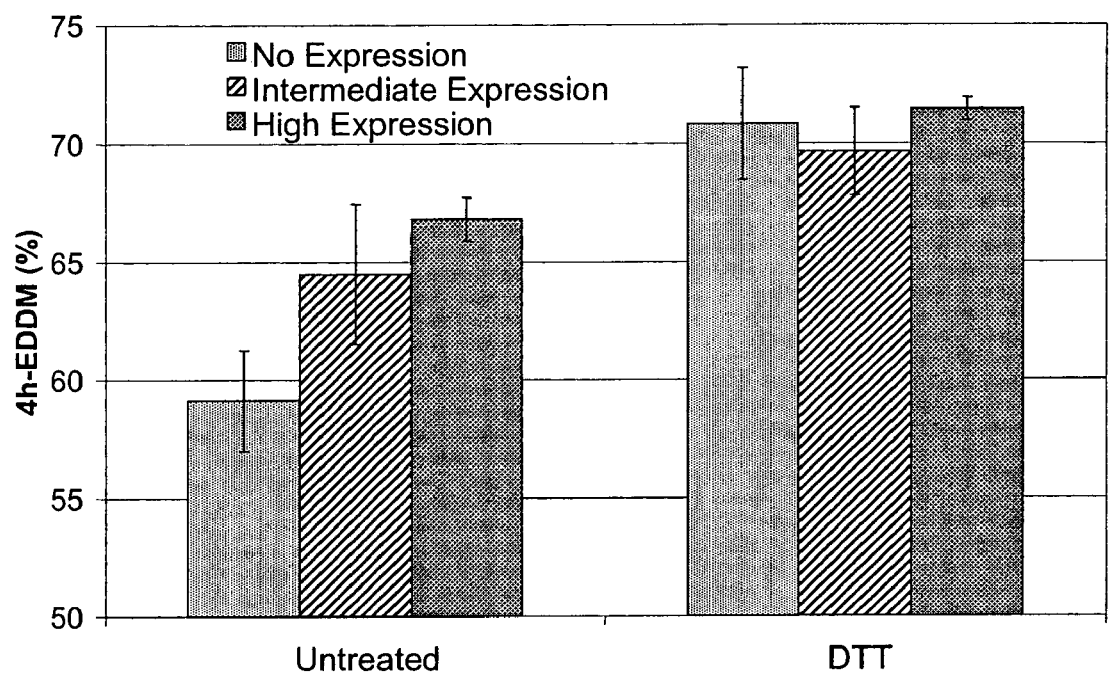
FIG. 3 is a graphical depiction of the digestibility of maize kernels which have been designated as displaying no expression, intermediate expression and high expression of NTR in endosperm based on the results of the Western dot blot analysis depicted in FIG. 2. The figure shows that, in the absence of dithiothreitol (DTT), the expression of NTR in kernels is positively correlated with the digestibility of the kernels.

When all three groups of kernels were pretreated with DTT, the digestibility of each group of kernels increased to approximately the same level (FIG. 3). This result suggests that it is possible to further reduce the disulfides in the kernel. Therefore, further increases in the digestibility can be expected with further increases in the expression of NTR and/or TRX.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleotide molecule comprising a nucleotide sequence selected from the group consisting of:
   (a) the nucleotide sequence set forth in SEQ ID NO: 24;
   (b) a nucleotide sequence encoding the amino acid sequence set forth in SEQ ID NO: 25;
   (c) a nucleotide sequence having at least 95% sequence identity to the coding sequence of the nucleotide sequence set forth in SEQ ID NO: 24, wherein said nucleotide sequence encodes a polypeptide comprising NADPH-thioredoxin reductase activity;
   (d) a nucleotide sequence that encodes a polypeptide comprising an amino acid sequence having at least 95% identity to the amino acid sequence set forth in SEQ ID NO: 25, wherein said polypeptide comprises NADPH-thioredoxin reductase activity; and
   (e) a nucleotide sequence that is complementary to the nucleotide sequence of (a), (b), (c), or (d).

2. An expression cassette comprising a nucleotide molecule, said nucleotide molecule comprising a nucleotide sequence selected from the group consisting of:
   (a) the nucleotide sequence set forth in SEQ ID NO: 24;
   (b) a nucleotide sequence encoding the amino acid sequence set forth in SEQ ID NO: 25;
   (c) a nucleotide sequence having at least 95% sequence identity to the coding sequence of the nucleotide sequence set forth in SEQ ID NO: 24, wherein said nucleotide sequence encodes a polypeptide comprising NADPH-thioredoxin reductase activity;
   (d) a nucleotide sequence that encodes a polypeptide comprising an amino acid sequence having at least 95% identity to the amino acid sequence set forth in SEQ ID NO: 25, wherein said polypeptide comprises NADPH-thioredoxin reductase activity; and
   (e) a nucleotide sequence that is complementary to the nucleotide sequence of (a), (b), (c), or (d);
wherein said nucleotide sequence is operably linked to a promoter.

3. A non-human host cell transformed with an expression cassette, said expression cassette comprising a nucleotide molecule, wherein said nucleotide molecule comprises a nucleotide sequence selected from the group consisting of:
   (a) the nucleotide sequence set forth in SEQ ID NO: 24;
   (b) a nucleotide sequence encoding the amino acid sequence set forth in SEQ ID NO: 25;
   (c) a nucleotide sequence having at least 95% sequence identity to the coding sequence of the nucleotide sequence set forth in SEQ ID NO: 24, wherein said nucleotide sequence encodes a polypeptide comprising NADPH-thioredoxin reductase activity;
   (d) a nucleotide sequence that encodes a polypeptide comprising an amino acid sequence having at least 95% identity to the amino acid sequence set forth in SEQ ID NO: 25, wherein said polypeptide comprises NADPH-thioredoxin reductase activity; and
   (e) a nucleotide sequence that is complementary to the nucleotide sequence of (a), (b), (c), or (d); and
wherein said nucleotide sequence is operably linked to a promoter.

4. The host cell of claim 3, wherein said host cell is a plant cell.

5. A transformed plant comprising in its genome at least one stably incorporated nucleotide construct comprising a promoter that drives expression in a plant cell operably linked to a nucleotide sequence, said nucleotide sequence selected from the group consisting of:
   (a) the nucleotide sequence set forth in SEQ ID NO: 24;
   (b) a nucleotide sequence encoding the amino acid sequence set forth in SEQ ID NO: 25;
   (c) a nucleotide sequence having at least 95%sequence identity to the coding sequence of the nucleotide sequence set forth in SEQ ID NO: 24, wherein said nucleotide sequence encodes a polypeptide comprising NADPH-thioredoxin reductase activity;
   (d) a nucleotide sequence that encodes a polypeptide comprising an amino acid sequence having at least 95% identity to the amino acid sequence set forth in SEQ ID NO: 25, wherein said polypeptide comprises NADPH-thioredoxin reductase activity; and
   (e) a nucleotide sequence that is complementary to the nucleotide sequence of (a), (b), (c), or (d).

6. The plant of claim 5, wherein said promoter is selected from the group consisting of seed-preferred, constitutive, chemically regulated, tissue-preferred, and developmentally regulated promoters.

7. The plant of claim 5, wherein said plant is a monocot or a dicot.

8. The plant of claim 7, wherein said monocot is selected from the group consisting of maize, wheat, rice, sorghum, barley, millet and rye.

9. The plant of claim 7, wherein said dicot is selected from the group consisting of soybean, *Brassica sp.*, alfalfa, safflower, sunflower, cotton, peanut and potato.

10. A transformed seed of a plant, said plant comprising in its genome at least one stably incorporated nucleotide construct comprising a promoter that drives expression in a plant cell operably linked a nucleotide sequence, said nucleotide sequence selected from the group consisting of:
   (a) the nucleotide sequence set forth in SEQ ID NO: 24;
   (b) a nucleotide sequence encoding the amino acid sequence set forth in SEQ ID NO: 25;
   (c) a nucleotide sequence having at least 95% sequence identity to the coding sequence of the nucleotide sequence set forth in SEQ ID NO: 24, wherein said nucleotide sequence encodes a polypeptide comprising NADPH-thioredoxin reductase activity;
   (d) a nucleotide sequence that encodes a polypeptide comprising an amino acid sequence having at least 95% identity to the amino acid sequence set forth in SEQ ID NO: 25, wherein said polypeptide comprises NADPH-thioredoxin reductase activity; and (e) a nucleotide sequence that is complementary to the nucleotide sequence of (a), (b), (c), or (d);

wherein said seed comprises said construct.

11. A method for altering the disulfide status of storage proteins in a plant or part thereof, said method comprising transforming said plant with a nucleotide construct comprising a promoter that drives expression in a plant cell operably linked to a nucleotide sequence encoding NADPH-thioredoxin reductase, wherein said nucleotide sequence is selected from the group consisting of:

(a) the nucleotide sequence set forth in SEQ ID NO:24;

(b) a nucleotide sequence encoding the amino acid sequence set forth in SEQ ID NO:25;

(c) a nucleotide sequence having at least 95% sequence identity to the coding sequence of the nucleotide sequence set forth in SEQ ID NO:24, wherein said nucleotide sequence encodes a polypeptide comprising NADPH-thioredoxin reductase activity;

(d) a nucleotide sequence that encodes a polypeptide comprising an amino acid sequence having at least 95% identity to the amino acid sequence set forth in SEQ ID NO:25, wherein said polypeptide comprises NADPH-thioredoxin reductase activity; and (e) a nucleotide sequence that is complementary to the nucleotide sequence of (a), (b), (c), or (d);

wherein said disulfide status of said storage proteins is altered in said plant or part thereof.

12. The method of claim 11, wherein said part is a seed or grain.

13. The method of claim 11, wherein said promoter is selected from the group consisting of seed-preferred, constitutive, chemically regulated, tissue-preferred, and developmentally regulated promoters.

14. A method for improving the digestibility of grain, said method comprising transforming a plant with a nucleotide construct comprising a promoter that drives expression in a plant cell operably linked to a nucleotide molecule, said nucleotide molecule comprising a nucleotide sequence selected from the group consisting of:

(a) the nucleotide sequence set forth in SEQ ID NO: 24;

(b) a nucleotide sequence encoding the amino acid sequence set forth in SEQ ID NO: 25;

(c) a nucleotide sequence having at least 95% sequence identity to the coding sequence of the nucleotide sequence set forth in SEQ ID NO: 24, wherein said nucleotide sequence encodes a polypeptide comprising NADPH-thioredoxin reductase activity;

(d) a nucleotide sequence that encodes a polypeptide comprising an amino acid sequence having at least 95% identity to the amino acid sequence set forth in SEQ ID NO: 25, wherein said polypeptide comprises NADPH-thioredoxin reductase activity; and (e) a nucleotide sequence that is complementary to the nucleotide sequence of (a), (b), (c), or (d);

wherein said nucleotide molecule is expressed in said grain and wherein said digestibility of said grain is increased when consumed by an animal.

15. The method of claim 14, wherein said promoter is selected from the group consisting of seed-preferred, constitutive, chemically regulated, tissue-preferred, and developmentally regulated promoters.

16. The method of claim 14, wherein said animal is selected from the group consisting of a human, a chicken, a cow, a pig, a turkey, a goat, a sheep, a dog, a cat and a fish.

17. The method of claim 14, wherein the grain is a mature maize kernel.

18. The method of claim 14, wherein the grain is a kernel that is part of whole plant corn harvested for silage.

19. A method for altering grain hardness, said method comprising transforming a plant with a nucleotide construct comprising a promoter that drives expression in a plant cell operably linked to a nucleotide molecule, said nucleotide molecule comprising a nucleotide sequence selected from the group consisting of:

(a) the nucleotide sequence set forth in SEQ ID NO: 24;

(b) a nucleotide sequence encoding the amino acid sequence set forth in SEQ ID NO: 25;

(c) a nucleotide sequence having at least 95% sequence identity to the coding sequence of the nucleotide sequence set forth in SEQ ID NO: 24, wherein said nucleotide sequence encodes a polypeptide comprising NADPH-thioredoxin reductase activity;

(d) a nucleotide sequence that encodes a polypeptide comprising an amino acid sequence having at least 95% identity to the amino acid sequence set forth in SEQ ID NO: 25, wherein said polypeptide comprises NADPH-thioredoxin reductase activity; and (e) a nucleotide sequence that is complementary to the nucleotide sequence of (a), (b), (c), or (d);

wherein said nucleotide molecule is expressed in said grain and wherein the hardness of said grain is decreased.

20. The method of claim 19, wherein said promoter is selected from the group consisting of seed-preferred, constitutive, chemically regulated, tissue-preferred, and developmentally regulated promoters.

21. The method of claim 19, wherein said grain hardness is decreased and the digestibility of said grain is increased when consumed by an animal.

22. A method for improving grain for processing, said method comprising transforming a plant with a nucleotide construct comprising a promoter that drives expression in a plant cell operably linked to a nucleotide molecule, said nucleotide molecule comprising a nucleotide sequence selected from the group consisting of:

(a) the nucleotide sequence set forth in SEQ ID NO: 24;

(b) a nucleotide sequence encoding the amino acid sequence set forth in SEQ ID NO: 25;

(c) a nucleotide sequence having at least 95% sequence identity to the coding sequence of the nucleotide sequence set forth in SEQ ID NO: 24, wherein said nucleotide sequence encodes a polypeptide comprising NADPH-thioredoxin reductase activity;

(d) a nucleotide sequence that encodes a polypeptide comprising an amino acid sequence having at least 95% identity to the amino acid sequence set forth in SEQ ID NO: 25, wherein said polypeptide comprises NADPH-thioredoxin reductase activity; and (e) a nucleotide sequence that is complementary to the nucleotide sequence of (a), (b), (c), or (d);

wherein said nucleotide molecule is expressed in said grain and wherein said grain is improved for processing.

23. The method of claim 22, wherein at least one of said promoters is selected from the group consisting of seed-preferred, constitutive, chemically regulated, tissue-preferred, and developmentally regulated promoters.

24. The method of claim 22, wherein the processing is wet milling and the improvement is increased starch extractability, decreased need for chemical reducing agents, or improved digestibility of wet milling by-products.

25. The method of claim 22, wherein the processing is grinding and the improvement is a higher degree of particle size reduction or energy savings.

26. The method of claim 22, wherein the processing is steam flaking and the improvement is a larger improvement in digestibility enhancement by steam flaking or energy savings.

27. The method of claim 22, wherein the processing is dry grind ethanol production and the improvement is increased fermentable starch or increased digestibility of fermentation by-products.

* * * * *

SEQUENCE LISTING

<160> NUMBER OF SEQ ID NOS: 25

<210> SEQ ID NO 1
<211> LENGTH: 797
<212> TYPE: DNA
<213> ORGANISM: Zea mays
<220> FEATURE:
<221> NAME/KEY: CDS
<222> LOCATION: (187)..(573)

<400> SEQUENCE: 1

```
gcacgagcat gtgtttccta gaaataatca atatattgag ataaatctca atcaatatat      60
tgattatttc taggaaacac atgccggaat gagggcacca ttatccgcgt ccagtgtgtc     120
cgctactccg ctcccccctca gtcctcagtt cctcacctag cggtagcgtg cgcgcgggag    180 acgtag atg gcg gct tcg gag gcg gca gcg gcg gcg gca aca ccg gtg       228
       Met Ala Ala Ser Glu Ala Ala Ala Ala Ala Thr Pro Val
       1               5                   10 acg ccg aca gag ggg acg gtg atc gcg atc cac agc ctg gag gag tgg      276
Thr Pro Thr Glu Gly Thr Val Ile Ala Ile His Ser Leu Glu Glu Trp
15              20                  25                  30 agc atc cag atc gag gag gcc aac agc gcc aag aag ctg gtg gtg att      324
Ser Ile Gln Ile Glu Glu Ala Asn Ser Ala Lys Lys Leu Val Val Ile
                35                  40                  45 gac ttc act gca aca tgg tgt cct ccg tgc cgc gcc atg gct cca att      372
Asp Phe Thr Ala Thr Trp Cys Pro Pro Cys Arg Ala Met Ala Pro Ile
            50                  55                  60 ttt gct gat atg gcc aag aag tcc cca aat gtt gtt ttc ctg aaa gtt      420
Phe Ala Asp Met Ala Lys Lys Ser Pro Asn Val Val Phe Leu Lys Val
65                  70                  75 gat gtg gat gaa atg aag acc att gct gag caa ttc agc gta gag gcc      468
Asp Val Asp Glu Met Lys Thr Ile Ala Glu Gln Phe Ser Val Glu Ala
80                  85                  90 atg cca aca ttc ctg ttc atg agg gag ggc gac gtc aag gac agg gtc      516
Met Pro Thr Phe Leu Phe Met Arg Glu Gly Asp Val Lys Asp Arg Val
95                  100                 105                 110 gtt ggc gca gca aag gaa gag cta gca agg aag ctt gaa cta cac atg      564
Val Gly Ala Ala Lys Glu Glu Leu Ala Arg Lys Leu Glu Leu His Met
                115                 120                 125 gcc tcg tag atcagtgatg ccgtaatgta gtattcgcct aaataagagg              613
Ala Ser acgcctcgcc tcaactctga gaaaactagt gcttctgtga tggtaattcg tatgagagag    673
tgccccattt ggtggtactt cttcgtatgt agtattaact cctgtcttaa tatgttgccc    733
tgcttgtgct tttcatacca tgtttgctct ttcagctgag gtgttaaaaa aaaaaaaaaa    793
aaaa                                                                 797
```

<210> SEQ ID NO 2
<211> LENGTH: 128
<212> TYPE: PRT
<213> ORGANISM: Zea mays

<400> SEQUENCE: 2

```
Met Ala Ala Ser Glu Ala Ala Ala Ala Ala Thr Pro Val Thr Pro
1               5                   10                  15

Thr Glu Gly Thr Val Ile Ala Ile His Ser Leu Glu Glu Trp Ser Ile
            20                  25                  30

Gln Ile Glu Glu Ala Asn Ser Ala Lys Lys Leu Val Val Ile Asp Phe
        35                  40                  45

Thr Ala Thr Trp Cys Pro Pro Cys Arg Ala Met Ala Pro Ile Phe Ala
    50                  55                  60

Asp Met Ala Lys Lys Ser Pro Asn Val Val Phe Leu Lys Val Asp Val
65                  70                  75                  80

Asp Glu Met Lys Thr Ile Ala Glu Gln Phe Ser Val Glu Ala Met Pro
                85                  90                  95

Thr Phe Leu Phe Met Arg Glu Gly Asp Val Lys Asp Arg Val Val Gly
```

```
                          100                 105                 110
Ala Ala Lys Glu Glu Leu Ala Arg Lys Leu Glu Leu His Met Ala Ser
        115                 120                 125

<210> SEQ ID NO 3
<211> LENGTH: 799
<212> TYPE: DNA
<213> ORGANISM: Zea mays
<220> FEATURE:
<221> NAME/KEY: CDS
<222> LOCATION: (69)..(455)

<400> SEQUENCE: 3
gtccgcgtcc agtgtgtccg ctcccccctca gtcctcacct agcggtagcg tgcgcgcggg      60 agacgtag atg gcg gct tcg gag gcg gcg gcg gcg gcg gcg aca ccg gtg     110
         Met Ala Ala Ser Glu Ala Ala Ala Ala Ala Ala Thr Pro Val
         1               5                   10 gcg ccg aca gag ggg acg gtg atc gcg atc cac agc ctg gag gag tgg     158
Ala Pro Thr Glu Gly Thr Val Ile Ala Ile His Ser Leu Glu Glu Trp
15                  20                  25                  30 agc atc cag atc gag gag gcc aac agc gcc aag aag ctg gtg gtg att     206
Ser Ile Gln Ile Glu Glu Ala Asn Ser Ala Lys Lys Leu Val Val Ile
                35                  40                  45 gac ttc act gca aca tgg tgt cct ccg tgc cgc gcc atg gct cca att     254
Asp Phe Thr Ala Thr Trp Cys Pro Pro Cys Arg Ala Met Ala Pro Ile
            50                  55                  60 ttt gct gat atg gcc aag aag tcc cca aat gtt gtt ttc ctg aaa gtt     302
Phe Ala Asp Met Ala Lys Lys Ser Pro Asn Val Val Phe Leu Lys Val
        65                  70                  75 gat gtc gat gaa atg aag acc att gct gag caa ttc agc gta gag gcc     350
Asp Val Asp Glu Met Lys Thr Ile Ala Glu Gln Phe Ser Val Glu Ala
    80                  85                  90 atg cca aca ttc ctg ttc atg agg gag ggc gac gtc aag gac agg gtc     398
Met Pro Thr Phe Leu Phe Met Arg Glu Gly Asp Val Lys Asp Arg Val
95                  100                 105                 110 gtt ggc gca gca aag gaa gag cta gca agg aag ctt gaa cta cac atg     446
Val Gly Ala Ala Lys Glu Glu Leu Ala Arg Lys Leu Glu Leu His Met
                115                 120                 125 gcc tcg tag atcagtgatg ccgtaatgta gtattcgcct aaataagagg            495
Ala Ser acgcctcgcc tcaactctga gaaaactagt gcttctgtga tggtaattcg tatgagagag     555 tgccccccttt ggtggtactt cttcgtatgt agtattaact cctgtcttaa tatgttgccc    615
tgcttgtgct tttcatacca tgtttgctct ttcagctgag gtgttatacg gtaaatcgga    675
gtcaatatct ttgaaattga ttaaaaaaaa aaaaaaaaaa aaaaaaaaaa aaaaaaaaaa    735
aaaaaaaaaa aaaaaaaaaa aaaaaaaaaa aaaaaaaaaa aaaaaaaaaa aaaaaaaaaa    795
aaaa                                                                 799

<210> SEQ ID NO 4
<211> LENGTH: 128
<212> TYPE: PRT
<213> ORGANISM: Zea mays

<400> SEQUENCE: 4

Met Ala Ala Ser Glu Ala Ala Ala Ala Ala Ala Thr Pro Val Ala Pro
1               5                   10                  15

Thr Glu Gly Thr Val Ile Ala Ile His Ser Leu Glu Glu Trp Ser Ile
            20                  25                  30
```

```
Gln Ile Glu Glu Ala Asn Ser Ala Lys Lys Leu Val Val Ile Asp Phe
         35                  40                  45

Thr Ala Thr Trp Cys Pro Pro Cys Arg Ala Met Ala Pro Ile Phe Ala
 50                  55                  60

Asp Met Ala Lys Lys Ser Pro Asn Val Val Phe Leu Lys Val Asp Val
 65                  70                  75                  80

Asp Glu Met Lys Thr Ile Ala Glu Gln Phe Ser Val Glu Ala Met Pro
                 85                  90                  95

Thr Phe Leu Phe Met Arg Glu Gly Asp Val Lys Asp Arg Val Val Gly
             100                 105                 110

Ala Ala Lys Glu Glu Leu Ala Arg Lys Leu Glu Leu His Met Ala Ser
             115                 120                 125
```

<210> SEQ ID NO 5
<211> LENGTH: 367
<212> TYPE: DNA
<213> ORGANISM: Zea mays
<220> FEATURE:
<221> NAME/KEY: CDS
<222> LOCATION: (3)..(194)

<400> SEQUENCE: 5

```
cc cgc ttc tcc gac gcc atc ttc gtc aag gtc gac gtc gac gag ctc        47
   Arg Phe Ser Asp Ala Ile Phe Val Lys Val Asp Val Asp Glu Leu
    1               5                  10                  15 gcg gag gtc gca agg aca tgg aag gta gag gcg atg cca acg ttc gta       95
Ala Glu Val Ala Arg Thr Trp Lys Val Glu Ala Met Pro Thr Phe Val
                 20                  25                  30 ctt gtc aag gat ggg aag gag gta agc cgt gtg gtt ggg gcc aag aag      143
Leu Val Lys Asp Gly Lys Glu Val Ser Arg Val Val Gly Ala Lys Lys
             35                  40                  45 gac gag ctt gag agg aag atc cgg atg ttc acg tca tct tcc tca tcg      191
Asp Glu Leu Glu Arg Lys Ile Arg Met Phe Thr Ser Ser Ser Ser Ser
         50                  55                  60 taa actcctgtgg ttcgcctggg acggagttgc tgaagtgaaa tggtcccttc           244
tctcaatgct gaaaaaggg ggaaaaacta tgtgaaaatg atggtagacg tgtctgggtc     304
agtaataaga gtttctaaaa tctgaatgag atttgaatcg ctttccgttg ctgaaaaaaa    364
aaa                                                                  367
```

<210> SEQ ID NO 6
<211> LENGTH: 63
<212> TYPE: PRT
<213> ORGANISM: Zea mays

<400> SEQUENCE: 6

```
Arg Phe Ser Asp Ala Ile Phe Val Lys Val Asp Val Asp Glu Leu Ala
 1               5                  10                  15

Glu Val Ala Arg Thr Trp Lys Val Glu Ala Met Pro Thr Phe Val Leu
                 20                  25                  30

Val Lys Asp Gly Lys Glu Val Ser Arg Val Val Gly Ala Lys Lys Asp
             35                  40                  45

Glu Leu Glu Arg Lys Ile Arg Met Phe Thr Ser Ser Ser Ser Ser
         50                  55                  60
```

<210> SEQ ID NO 7
<211> LENGTH: 720
<212> TYPE: DNA
<213> ORGANISM: Zea mays
<220> FEATURE:

```
<221> NAME/KEY: CDS
<222> LOCATION: (38)..(442)

<400> SEQUENCE: 7
aggcagcgag tgcaaacaac cgcgagagcg atcagcg atg ggc tcc ttc ttc tcg       55
                                          Met Gly Ser Phe Phe Ser
                                          1               5 acc tta gtg acg ccc cct ccg ccc gcc gcc gac gac ccg aac tgc gcc       103
Thr Leu Val Thr Pro Pro Pro Pro Ala Ala Asp Asp Pro Asn Cys Ala
            10                  15                  20 gtg gtg gcc gcg cac tcc aag gcc acc tac gac gag cag tgg gcg gcc       151
Val Val Ala Ala His Ser Lys Ala Thr Tyr Asp Glu Gln Trp Ala Ala
        25                  30                  35 cac aag agc agc agc aag ctg atg gtg atc gac ttc tcg gcg tcc tgg       199
His Lys Ser Ser Ser Lys Leu Met Val Ile Asp Phe Ser Ala Ser Trp
    40                  45                  50 tgc ggg ccc tgc cgc ttc atc gag ccg gcc ttc aag gag ctg gcc tcc       247
Cys Gly Pro Cys Arg Phe Ile Glu Pro Ala Phe Lys Glu Leu Ala Ser
55                  60                  65                  70 cgc ttc acc gat gcc atc ttc atc aag gtc gac gtc gac gag ctc gcg       295
Arg Phe Thr Asp Ala Ile Phe Ile Lys Val Asp Val Asp Glu Leu Ala
                75                  80                  85 gag gtc gca agg aca tgg aag gta gag gcg atg cca acg ttc gtg ctg       343
Glu Val Ala Arg Thr Trp Lys Val Glu Ala Met Pro Thr Phe Val Leu
            90                  95                  100 gtc aag gat ggg aag gag gta ggc cgt gtg att ggg gct aag aag gac       391
Val Lys Asp Gly Lys Glu Val Gly Arg Val Ile Gly Ala Lys Lys Asp
        105                 110                 115 gag ctt gag agg aag atc agg atg ttc gtc acg tca tct tcc tcg tcc       439
Glu Leu Glu Arg Lys Ile Arg Met Phe Val Thr Ser Ser Ser Ser Ser
    120                 125                 130 taa cttagcagtg catacactcc caccttatta ctggtttctc gactccagtg           492
gttcgcctgg gacggggttg ctgaaatggt tcccttctct gaatactgaa aaatcaaaaa    552
aagaagtata tgaaaaaatg atggtagacg tgtctgggtc aataagagtt tctgaaactt    612
ggatttgtat gtgtcagtct ctgtgttctg tttccaagga atggatcatg tgagtttgga    672
atatagctgg aaatatgttg tgctgttaaa aaaaaaaaaa aaaaaaaa                 720

<210> SEQ ID NO 8
<211> LENGTH: 134
<212> TYPE: PRT
<213> ORGANISM: Zea mays

<400> SEQUENCE: 8

Met Gly Ser Phe Phe Ser Thr Leu Val Thr Pro Pro Pro Ala Ala
1               5                   10                  15

Asp Asp Pro Asn Cys Ala Val Val Ala Ala His Ser Lys Ala Thr Tyr
            20                  25                  30

Asp Glu Gln Trp Ala Ala His Lys Ser Ser Ser Lys Leu Met Val Ile
        35                  40                  45

Asp Phe Ser Ala Ser Trp Cys Gly Pro Cys Arg Phe Ile Glu Pro Ala
    50                  55                  60

Phe Lys Glu Leu Ala Ser Arg Phe Thr Asp Ala Ile Phe Ile Lys Val
65                  70                  75                  80

Asp Val Asp Glu Leu Ala Glu Val Ala Arg Thr Trp Lys Val Glu Ala
                85                  90                  95

Met Pro Thr Phe Val Leu Val Lys Asp Gly Lys Glu Val Gly Arg Val
            100                 105                 110
```

```
Ile Gly Ala Lys Lys Asp Glu Leu Glu Arg Lys Ile Arg Met Phe Val
        115                 120                 125

Thr Ser Ser Ser Ser Ser
    130

<210> SEQ ID NO 9
<211> LENGTH: 722
<212> TYPE: DNA
<213> ORGANISM: Zea mays
<220> FEATURE:
<221> NAME/KEY: CDS
<222> LOCATION: (84)..(455)

<400> SEQUENCE: 9
agcaatcttg caatccaccc ctcgaaagaa aacctcaatc aacaccagca gctctcgatc      60
ccaccgagga agaagagaga gga atg gcg tcc gag gag gaa gga gtc gtg atc    113
                        Met Ala Ser Glu Glu Glu Gly Val Val Ile
                          1               5                  10 gcc tgc cac acc aag gcc gac ttc gac gcc cac atg gcc aag gcc aag    161
Ala Cys His Thr Lys Ala Asp Phe Asp Ala His Met Ala Lys Ala Lys
             15                  20                  25 gag gcc ggc aag ctg gtg atc att gac ttc acg gcc tcc tgg tgc ggc    209
Glu Ala Gly Lys Leu Val Ile Ile Asp Phe Thr Ala Ser Trp Cys Gly
         30                  35                  40 ccc tgc cgc ttc atc gcg cca ctg ttc gtc gag cac gcc aag aag ttc    257
Pro Cys Arg Phe Ile Ala Pro Leu Phe Val Glu His Ala Lys Lys Phe
     45                  50                  55 acc cag gct gtg ttc ctg aag gtg gac gtg gac gag ctg aag gaa gtt    305
Thr Gln Ala Val Phe Leu Lys Val Asp Val Asp Glu Leu Lys Glu Val
 60                  65                  70 gcc gcg gcc tac gat gtc gag gcg atg ccg acc ttc cac ttc gtc aag    353
Ala Ala Ala Tyr Asp Val Glu Ala Met Pro Thr Phe His Phe Val Lys
75                  80                  85                  90 aac ggg gtg acg gtc gag acc gtc gtc ggt gcc agg aag gag aac ctc    401
Asn Gly Val Thr Val Glu Thr Val Val Gly Ala Arg Lys Glu Asn Leu
                 95                 100                 105 ctg gcc cag atc gag aag cac tgc gcc gcg gcc gtg cct gct gcg tct    449
Leu Ala Gln Ile Glu Lys His Cys Ala Ala Val Pro Ala Ala Ser
             110                 115                 120 gcg tag agaggatgga ccagcacgtg gcggtggcgg tggcggttgt cttgtcgttt    505
Ala tcagtttggg cttgtcagct gtggctgggt ggttgattgt gaactggagc atgcagtttt    565
actctgggag cccatcattt ggttggctca ggtgtcaata atctgtatac cttaatcatg    625
gatagttgtt gtgagttgtg attggacttt ggaatttgga tgtctggctt cgttctgtta    685
tgatgatgat gatggattga aaaaaaaaaa aaaaaaa                              722

<210> SEQ ID NO 10
<211> LENGTH: 123
<212> TYPE: PRT
<213> ORGANISM: Zea mays

<400> SEQUENCE: 10

Met Ala Ser Glu Glu Glu Gly Val Val Ile Ala Cys His Thr Lys Ala
  1               5                  10                  15

Asp Phe Asp Ala His Met Ala Lys Ala Lys Glu Ala Gly Lys Leu Val
             20                  25                  30

Ile Ile Asp Phe Thr Ala Ser Trp Cys Gly Pro Cys Arg Phe Ile Ala
         35                  40                  45
```

```
Pro Leu Phe Val Glu His Ala Lys Lys Phe Thr Gln Ala Val Phe Leu
        50                  55                  60

Lys Val Asp Val Asp Glu Leu Lys Glu Val Ala Ala Ala Tyr Asp Val
65                  70                  75                  80

Glu Ala Met Pro Thr Phe His Phe Val Lys Asn Gly Val Thr Val Glu
                85                  90                  95

Thr Val Val Gly Ala Arg Lys Glu Asn Leu Leu Ala Gln Ile Glu Lys
            100                 105                 110

His Cys Ala Ala Ala Val Pro Ala Ala Ser Ala
        115                 120

<210> SEQ ID NO 11
<211> LENGTH: 727
<212> TYPE: DNA
<213> ORGANISM: Zea mays
<220> FEATURE:
<221> NAME/KEY: CDS
<222> LOCATION: (84)..(452)

<400> SEQUENCE: 11
cccacgcgtc cgcggacgcg tgggcttgca atcacaacga acaaaagctc tcgatctcac      60
cgacaccgag gaagaagaga tca atg gcg tcc gag cag gga gtc gtg atc gcg     113
                          Met Ala Ser Glu Gln Gly Val Val Ile Ala
                          1               5                    10 tgc cac agc aag gct gag ttt gac gcc cac atg acc aag gcc cag gaa        161
Cys His Ser Lys Ala Glu Phe Asp Ala His Met Thr Lys Ala Gln Glu
            15                  20                  25 gcc ggc aag ctg gtg gtc att gac ttc act gcc gcc tgg tgc ggt cca        209
Ala Gly Lys Leu Val Val Ile Asp Phe Thr Ala Ala Trp Cys Gly Pro
        30                  35                  40 tgc cgc gcc atc gcc cca ctg ttc gtc gaa cac gcc aag aag ttc act        257
Cys Arg Ala Ile Ala Pro Leu Phe Val Glu His Ala Lys Lys Phe Thr
    45                  50                  55 cag gtc gtc ttc ctg aag gtg gac gtg gac gaa gtg aag gaa gtc acc        305
Gln Val Val Phe Leu Lys Val Asp Val Asp Glu Val Lys Glu Val Thr
60                  65                  70 gcg gcc tac gag gtc gag gcg atg ccg acc ttc cac ttc gtc aag aac        353
Ala Ala Tyr Glu Val Glu Ala Met Pro Thr Phe His Phe Val Lys Asn
75                  80                  85                  90 ggc aag acg gtc gcg acc atc gtg ggt gcc aag aag gac gag ctc ctg        401
Gly Lys Thr Val Ala Thr Ile Val Gly Ala Lys Lys Asp Glu Leu Leu
                95                  100                 105 gcc cag atc gag aag cat gcc gcg cct gcg cct gcg tct gcg tct gcc        449
Ala Gln Ile Glu Lys His Ala Ala Pro Ala Pro Ala Ser Ala Ser Ala
            110                 115                 120 taa aggagatcag atcagtcgtc gccgtcaata agggccagca cgtatggctg              502
taaatgttgt cgttatcagt tctggctttg tcgtttgtgg gcgattgtga actagtagta      562
tgtttgtttc tatccgagcc ggaggcgata cttaaccatg gatacttgtt gtgagttcgt      622
ttctgttcgc gtgtgactct tgaattgaat caaccagctc accactgcac caggccgtgg      682
tgagtggtga cagtgatttc ctgttaaaaa aaaaaaaaaa aaaaa                      727

<210> SEQ ID NO 12
<211> LENGTH: 122
<212> TYPE: PRT
<213> ORGANISM: Zea mays

<400> SEQUENCE: 12
```

```
Met Ala Ser Glu Gln Gly Val Val Ile Ala Cys His Ser Lys Ala Glu
1               5                   10                  15

Phe Asp Ala His Met Thr Lys Ala Gln Glu Ala Gly Lys Leu Val Val
            20                  25                  30

Ile Asp Phe Thr Ala Ala Trp Cys Gly Pro Cys Arg Ala Ile Ala Pro
        35                  40                  45

Leu Phe Val Glu His Ala Lys Lys Phe Thr Gln Val Val Phe Leu Lys
    50                  55                  60

Val Asp Val Asp Glu Val Lys Glu Val Thr Ala Ala Tyr Glu Val Glu
65                  70                  75                  80

Ala Met Pro Thr Phe His Phe Val Lys Asn Gly Lys Thr Val Ala Thr
                85                  90                  95

Ile Val Gly Ala Lys Lys Asp Glu Leu Leu Ala Gln Ile Glu Lys His
            100                 105                 110

Ala Ala Pro Ala Pro Ala Ser Ala Ser Ala
        115                 120

<210> SEQ ID NO 13
<211> LENGTH: 700
<212> TYPE: DNA
<213> ORGANISM: Zea mays
<220> FEATURE:
<221> NAME/KEY: CDS
<222> LOCATION: (41)..(421)

<400> SEQUENCE: 13
ggatcccaca ccgaggaaag gagaagagag ggtcggaata atg gcg gcc gag gag      55
                                             Met Ala Ala Glu Glu
                                             1               5 ggt gcc gtg atc gcg tgc cac acc aag gac gag ttc gac gcc cgc atg    103
Gly Ala Val Ile Ala Cys His Thr Lys Asp Glu Phe Asp Ala Arg Met
            10                  15                  20 gcc aag gcc aag gag cag ggc aag ctg gtg gtc atc gac ttc atg gcc    151
Ala Lys Ala Lys Glu Gln Gly Lys Leu Val Val Ile Asp Phe Met Ala
        25                  30                  35 ccc tgg tgc agt ggg tgc cag atg atg gcc ccg gtg tac gcg gac tgc    199
Pro Trp Cys Ser Gly Cys Gln Met Met Ala Pro Val Tyr Ala Asp Cys
    40                  45                  50 gcc agc aag tac cct tcc gcg gtc ttc ctc gag gtc gac gtc gac gaa    247
Ala Ser Lys Tyr Pro Ser Ala Val Phe Leu Glu Val Asp Val Asp Glu
55                  60                  65 ctg ctg gaa gtc gcg aag atc tac ggc gtc cat gtg atg ccg acc ttc    295
Leu Leu Glu Val Ala Lys Ile Tyr Gly Val His Val Met Pro Thr Phe
70                  75                  80                  85 tgc ttc atc agg aac ggc gag acg ctc gag agc ttt gct acc gtc gac    343
Cys Phe Ile Arg Asn Gly Glu Thr Leu Glu Ser Phe Ala Thr Val Asp
                90                  95                  100 gag gac gag ctc cgg gac gcc gtc agg aag tac gcc gcc gct ggc act    391
Glu Asp Glu Leu Arg Asp Ala Val Arg Lys Tyr Ala Ala Ala Gly Thr
            105                 110                 115 acg acg gct cct gcc tcg gcg tcc gcc taa ttcaggagat gtgatgtgta      441
Thr Thr Ala Pro Ala Ser Ala Ser Ala
        120                 125 gcaaatagcg cgcgcgcacc agtcgtcaat aaataaataa ataaataaat aaataaataa    501
ataaataaat aaaggccaac gtacgacgac aaattagtgg cgcgcgcggt agtagctagc    561
agagtatgcg ccgccactgt gtcgatctgc agtttggtcg tttaaaagtg attgtagtgt    621
gtactatgtt cagctcgaaa aaaaaaaaaa aaaaaaaaaa aaaaaaaaaa aaaaaaaaa     681
```
aaaaaaaaaa aaaaaaaa                                                          700

<210> SEQ ID NO 14
<211> LENGTH: 126
<212> TYPE: PRT
<213> ORGANISM: Zea mays

<400> SEQUENCE: 14

Met Ala Glu Glu Gly Ala Val Ile Ala Cys His Thr Lys Asp Glu
1               5                   10                  15

Phe Asp Ala Arg Met Ala Lys Ala Lys Glu Gln Gly Lys Leu Val Val
            20                  25                  30

Ile Asp Phe Met Ala Pro Trp Cys Ser Gly Cys Gln Met Met Ala Pro
        35                  40                  45

Val Tyr Ala Asp Cys Ala Ser Lys Tyr Pro Ser Ala Val Phe Leu Glu
    50                  55                  60

Val Asp Val Asp Glu Leu Leu Glu Val Ala Lys Ile Tyr Gly Val His
65                  70                  75                  80

Val Met Pro Thr Phe Cys Phe Ile Arg Asn Gly Glu Thr Leu Glu Ser
                85                  90                  95

Phe Ala Thr Val Asp Glu Asp Glu Leu Arg Asp Ala Val Arg Lys Tyr
            100                 105                 110

Ala Ala Ala Gly Thr Thr Thr Ala Pro Ala Ser Ala Ser Ala
        115                 120                 125

<210> SEQ ID NO 15
<211> LENGTH: 658
<212> TYPE: DNA
<213> ORGANISM: Hordeum vulgare
<220> FEATURE:
<221> NAME/KEY: CDS
<222> LOCATION: (52)..(420)

<400> SEQUENCE: 15
aaagtgcgcg tgagaaataa gccgagtaga gagagagaga gagagagaga g atg gcg      57
                                                          Met Ala
                                                          1 gcg tcg gca acg gcg gcg gca gtg gcg gcg gag gtg atc tcg gtc cac     105
Ala Ser Ala Thr Ala Ala Ala Val Ala Ala Glu Val Ile Ser Val His
    5                   10                  15 agc ctg gag cag tgg acc atg cag atc gag gag gcc aac acc gcc aag     153
Ser Leu Glu Gln Trp Thr Met Gln Ile Glu Glu Ala Asn Thr Ala Lys
        20                  25                  30 aag ctg gtg gtg att gac ttc act gca tca tgg tgc gga cca tgc cgc     201
Lys Leu Val Val Ile Asp Phe Thr Ala Ser Trp Cys Gly Pro Cys Arg
35                  40                  45                  50 atc atg gct cca gtt ttc gct gat ctc gcc aag aag ttc cca aat gct     249
Ile Met Ala Pro Val Phe Ala Asp Leu Ala Lys Lys Phe Pro Asn Ala
                55                  60                  65 gtt ttc ctc aag gtc gac gtg gat gaa ctg aag ccc att gct gag caa     297
Val Phe Leu Lys Val Asp Val Asp Glu Leu Lys Pro Ile Ala Glu Gln
            70                  75                  80 ttc agt gtc gag gcc atg cca acg ttc ctg ttc atg aag gaa gga gac     345
Phe Ser Val Glu Ala Met Pro Thr Phe Leu Phe Met Lys Glu Gly Asp
        85                  90                  95 gtc aag gac agg gtt gtc gga gct atc aag gag gaa ctg acc gcc aag     393
Val Lys Asp Arg Val Val Gly Ala Ile Lys Glu Glu Leu Thr Ala Lys
    100                 105                 110 gtt ggg ctt cac gcg gcg gcc cag taa ttacctattg gtgtagtatt           440
Val Gly Leu His Ala Ala Ala Gln -continued

```
         115                 120
cgcctaaata aaattgccgc tcaagaagac tatgaatgct gtgtactgct tgctacttgt    500
tgttggttta tggatactgc gatgcttgat ccaagctagt gtgcttttgc atatggttaa    560
ccaaaacagg attgctaaat cttagtcgac tgagatttaa ccaagtctta gtcaaagcta    620
tattggcgtg atcttacgta aaaaaaaaaa aaaaaaa                             658
```

<210> SEQ ID NO 16
<211> LENGTH: 122
<212> TYPE: PRT
<213> ORGANISM: Hordeum vulgare

<400> SEQUENCE: 16

```
Met Ala Ser Ala Thr Ala Ala Val Ala Glu Val Ile Ser
1               5                   10                  15

Val His Ser Leu Glu Gln Trp Thr Met Gln Ile Glu Glu Ala Asn Thr
                20                  25                  30

Ala Lys Lys Leu Val Val Ile Asp Phe Thr Ala Ser Trp Cys Gly Pro
            35                  40                  45

Cys Arg Ile Met Ala Pro Val Phe Ala Asp Leu Ala Lys Lys Phe Pro
        50                  55                  60

Asn Ala Val Phe Leu Lys Val Asp Val Asp Glu Leu Lys Pro Ile Ala
65                  70                  75                  80

Glu Gln Phe Ser Val Glu Ala Met Pro Thr Phe Leu Phe Met Lys Glu
                85                  90                  95

Gly Asp Val Lys Asp Arg Val Val Gly Ala Ile Lys Glu Glu Leu Thr
                100                 105                 110

Ala Lys Val Gly Leu His Ala Ala Ala Gln
            115                 120
```

<210> SEQ ID NO 17
<211> LENGTH: 580
<212> TYPE: DNA
<213> ORGANISM: Zea mays
<220> FEATURE:
<221> NAME/KEY: misc_feature
<223> OTHER INFORMATION: "n" at position 116, 118, 120, 125, 127, 317,
      331, 434, 473, 482, 486, 493, 501, 507, 515, 519, 532, 542, and
      579 can be an a, c, g, or t

<400> SEQUENCE: 17

```
tcggatccca caccgaggaa aaggagaaga gagcgagggt cggaataatg gcggccgagg    60
agggtgccgt gatcgcgtgc cacaccaagg acgagttcga cgcccgcatg gccaangncn    120
aggancnggc aagctggtgg tcatcgactt catggccccc tggtgcagtg ggtgccagat    180
gatggccccg gtgtacgcgg actgcgccag caagtaccct tccgcggtct cctcgaggt     240 cgacgtggac gaactgctgg aagtcgcgaa gatctacggc gtccatgtga tgccgacctt    300
ctgcttcatc aggaacngcg agacgctcga nagctttgct accgtcgacg aagacgagct    360
ccgggacgcc gtcaggaagt acgccgccgc tggcactacg acgctcctgc ctcggcgtcc    420
gcctaattca gganatgtga tgtgtagcaa atagcgcgcg cgcaccatcg tcnataaata    480
antaantaat aantaattaa ntaantnaag ggcncgtnc aacaacaatt tntggccccg     540
cngtattact acaaatttgc cccccctgtt tcatctgcnt                          580
```

<210> SEQ ID NO 18
<211> LENGTH: 590
<212> TYPE: DNA

```
<213> ORGANISM: Zea mays
<220> FEATURE:
<221> NAME/KEY: CDS
<222> LOCATION: (60)..(425)
<220> FEATURE:
<221> NAME/KEY: misc_feature
<223> OTHER INFORMATION: "n" at position 9, 493, 537, 548, 581, and 584
      can be an a, c, g, or t

<400> SEQUENCE: 18
gttgcaatna caacgaacag aagctctcga tctcaccgac accgaggaag aagagatca         59 atg gcg tcc gag cag gga gtc gtg atc gcg tgc cac agc aag gct gag        107
Met Ala Ser Glu Gln Gly Val Val Ile Ala Cys His Ser Lys Ala Glu
1               5                  10                  15 ttc gac gcc cac atg acc aag gcc cag gaa gcc ggc aag ctg gtg gtc        155
Phe Asp Ala His Met Thr Lys Ala Gln Glu Ala Gly Lys Leu Val Val
            20                  25                  30 atc gac ttc act gcc gcc tgg tgc ggt cca tgc cgc gcc atc gcc cca        203
Ile Asp Phe Thr Ala Ala Trp Cys Gly Pro Cys Arg Ala Ile Ala Pro
        35                  40                  45 ctg ttc gtc gaa cac gcc aag aag ttc act cag gtc gtc ttc ctg aag        251
Leu Phe Val Glu His Ala Lys Lys Phe Thr Gln Val Val Phe Leu Lys
    50                  55                  60 gtg gac gtg gac gaa gtg aag gaa gtc acc gcg gcc tac gag gtc gag        299
Val Asp Val Asp Glu Val Lys Glu Val Thr Ala Ala Tyr Glu Val Glu
65                  70                  75                  80 gcg atg ccg acc ttc cac ttc gtc aag aac ggc aag acg gtc gcg acc        347
Ala Met Pro Thr Phe His Phe Val Lys Asn Gly Lys Thr Val Ala Thr
                85                  90                  95 atc gtg ggt gcc agg aag gac gag ctc ctg gcc cag atc gag aag cat        395
Ile Val Gly Ala Arg Lys Asp Glu Leu Leu Ala Gln Ile Glu Lys His
            100                 105                 110 gcc gcg cct gcg cct gcg tct gcg tct gcc taaaggagat cagtcgtcgc          445
Ala Ala Pro Ala Pro Ala Ser Ala Ser Ala
        115                 120 cgtcaataag ggccagcacg tatggctgta aatgttgtcg ttatcagntc tggctttgtc       505
gtttgtgggc gattgtgaac tagtagtatg tnggttctat ccnaagccgg aggcgatctt       565
aacctgggat acttgntgng aaaaa                                             590

<210> SEQ ID NO 19
<211> LENGTH: 122
<212> TYPE: PRT
<213> ORGANISM: Zea mays
<220> FEATURE:
<221> NAME/KEY: misc_feature
<223> OTHER INFORMATION: "n" at position 9, 493, 537, 548, 581, and 584
      can be an a, c, g, or t

<400> SEQUENCE: 19

Met Ala Ser Glu Gln Gly Val Val Ile Ala Cys His Ser Lys Ala Glu
1               5                  10                  15

Phe Asp Ala His Met Thr Lys Ala Gln Glu Ala Gly Lys Leu Val Val
            20                  25                  30

Ile Asp Phe Thr Ala Ala Trp Cys Gly Pro Cys Arg Ala Ile Ala Pro
        35                  40                  45

Leu Phe Val Glu His Ala Lys Lys Phe Thr Gln Val Val Phe Leu Lys
    50                  55                  60

Val Asp Val Asp Glu Val Lys Glu Val Thr Ala Ala Tyr Glu Val Glu
65                  70                  75                  80

Ala Met Pro Thr Phe His Phe Val Lys Asn Gly Lys Thr Val Ala Thr
```

-continued

```
                     85                  90                  95
Ile Val Gly Ala Arg Lys Asp Glu Leu Leu Ala Gln Ile Glu Lys His
                100                 105                 110

Ala Ala Pro Ala Pro Ala Ser Ala Ser Ala
        115                 120

<210> SEQ ID NO 20
<211> LENGTH: 948
<212> TYPE: DNA
<213> ORGANISM: Zea mays
<220> FEATURE:
<221> NAME/KEY: CDS
<222> LOCATION: (3)..(737)

<400> SEQUENCE: 20 cc aag atc ctc acc gag acc gtc acc acc gtg gac ttc tcc gcc cgc        47
   Lys Ile Leu Thr Glu Thr Val Thr Thr Val Asp Phe Ser Ala Arg
    1               5                  10                  15 ccc ttc cgt gtc gcc tcc gac gac acc gtt gtg cac gcc gac tcc gtc       95
Pro Phe Arg Val Ala Ser Asp Asp Thr Val Val His Ala Asp Ser Val
             20                  25                  30 gtc gtc gcc acg ggc gcc gtc gcg cgc agg ctg cac ttc gcc ggc tcc      143
Val Val Ala Thr Gly Ala Val Ala Arg Arg Leu His Phe Ala Gly Ser
         35                  40                  45 gac gcc ttc tgg aac cgg ggc atc tcc gcc tgc gcc gtc tgc gac ggg      191
Asp Ala Phe Trp Asn Arg Gly Ile Ser Ala Cys Ala Val Cys Asp Gly
 50                  55                  60 gct gcg cct atc ttc cgg aac aag ccc atc gcc gtc gtc gga ggc ggg      239
Ala Ala Pro Ile Phe Arg Asn Lys Pro Ile Ala Val Val Gly Gly Gly
     65                  70                  75 gac tcc gcc atg gag gag gct aac ttc ctc acc aag tac ggc tcg caa      287
Asp Ser Ala Met Glu Glu Ala Asn Phe Leu Thr Lys Tyr Gly Ser Gln
 80                  85                  90                  95 gtt tac atc atc cac cgc cgc agc gac ttc cgg gcg tcc aag atc atg      335
Val Tyr Ile Ile His Arg Arg Ser Asp Phe Arg Ala Ser Lys Ile Met
            100                 105                 110 cag gcg cgc acg ctc tcc aac ccc aag atc aag gtc gtc tgg aac tcc      383
Gln Ala Arg Thr Leu Ser Asn Pro Lys Ile Lys Val Val Trp Asn Ser
        115                 120                 125 gag gtc gtc gag gcc tac ggc ggt gcg gat ggc ggc ccg cta gcc ggc      431
Glu Val Val Glu Ala Tyr Gly Gly Ala Asp Gly Gly Pro Leu Ala Gly
    130                 135                 140 gtc aag gtc aag gac gtc gtc acc ggc gag gtc tct gat ctc cag gtg      479
Val Lys Val Lys Asp Val Val Thr Gly Glu Val Ser Asp Leu Gln Val
145                 150                 155 gcc ggg ctc ttc ttt gcc atc ggt cac gag ccg gcg aca aaa ttt ctt      527
Ala Gly Leu Phe Phe Ala Ile Gly His Glu Pro Ala Thr Lys Phe Leu
160                 165                 170                 175 gga ggg cag ctc gag ctc gac tct gat ggg tat gtg gtg acc aag ccc      575
Gly Gly Gln Leu Glu Leu Asp Ser Asp Gly Tyr Val Val Thr Lys Pro
                180                 185                 190 ggt tcc acg cac acc agt gtg cag ggg gtc ttt gca gct ggg gat gtc      623
Gly Ser Thr His Thr Ser Val Gln Gly Val Phe Ala Ala Gly Asp Val
            195                 200                 205 cag gac aag aag tac cgc cag gcc att act gca gct gga tca ggt tgc      671
Gln Asp Lys Lys Tyr Arg Gln Ala Ile Thr Ala Ala Gly Ser Gly Cys
        210                 215                 220 atg gct gct ctg gat gca gag cac tac ctg cag gag gtt gga gca cag      719
Met Ala Ala Leu Asp Ala Glu His Tyr Leu Gln Glu Val Gly Ala Gln
225                 230                 235
```

```
gaa ggg aag acc gat tga ctatgtctgg gccaagctgc tcttgggcca        767
Glu Gly Lys Thr Asp
240 aggaaaactt ctccgaaagc cgctctctag tggtgtaaac agcacattat tatttggttt    827 taggcctcaa attacgttac attggaaatt gatttatatg agcgtgcgca agcttgtata    887 cattattcgc attgtttatt actcttagag tcttagtcat taatcacact ttgctaaaaa    947 a                                                                    948
```

<210> SEQ ID NO 21
<211> LENGTH: 244
<212> TYPE: PRT
<213> ORGANISM: Zea mays

<400> SEQUENCE: 21

```
Lys Ile Leu Thr Glu Thr Val Thr Thr Val Asp Phe Ser Ala Arg Pro
1               5                   10                  15

Phe Arg Val Ala Ser Asp Asp Thr Val Val His Ala Asp Ser Val Val
                20                  25                  30

Val Ala Thr Gly Ala Val Ala Arg Arg Leu His Phe Ala Gly Ser Asp
            35                  40                  45

Ala Phe Trp Asn Arg Gly Ile Ser Ala Cys Ala Val Cys Asp Gly Ala
        50                  55                  60

Ala Pro Ile Phe Arg Asn Lys Pro Ile Ala Val Val Gly Gly Gly Asp
65                  70                  75                  80

Ser Ala Met Glu Glu Ala Asn Phe Leu Thr Lys Tyr Gly Ser Gln Val
                85                  90                  95

Tyr Ile Ile His Arg Arg Ser Asp Phe Arg Ala Ser Lys Ile Met Gln
                100                 105                 110

Ala Arg Thr Leu Ser Asn Pro Lys Ile Lys Val Val Trp Asn Ser Glu
            115                 120                 125

Val Val Glu Ala Tyr Gly Gly Ala Asp Gly Gly Pro Leu Ala Gly Val
        130                 135                 140

Lys Val Lys Asp Val Val Thr Gly Glu Val Ser Asp Leu Gln Val Ala
145                 150                 155                 160

Gly Leu Phe Phe Ala Ile Gly His Glu Pro Ala Thr Lys Phe Leu Gly
                165                 170                 175

Gly Gln Leu Glu Leu Asp Ser Asp Gly Tyr Val Val Thr Lys Pro Gly
                180                 185                 190

Ser Thr His Thr Ser Val Gln Gly Val Phe Ala Ala Gly Asp Val Gln
            195                 200                 205

Asp Lys Lys Tyr Arg Gln Ala Ile Thr Ala Ala Gly Ser Gly Cys Met
        210                 215                 220

Ala Ala Leu Asp Ala Glu His Tyr Leu Gln Glu Val Gly Ala Gln Glu
225                 230                 235                 240

Gly Lys Thr Asp
```

<210> SEQ ID NO 22
<211> LENGTH: 556
<212> TYPE: DNA
<213> ORGANISM: Zea mays
<220> FEATURE:
<221> NAME/KEY: CDS
<222> LOCATION: (1)..(336)

<400> SEQUENCE: 22

```
ggc ggt gcg gat ggc ggc ccg cta gcc ggc gtc aag gtc aag gac gtc    48
```

```
Gly Gly Ala Asp Gly Gly Pro Leu Ala Gly Val Lys Val Lys Asp Val
1               5                   10                  15 gtc acc ggc gag gtc tct gat ctc cag gtg gcc ggg ctc ttc ttt gcc      96
Val Thr Gly Glu Val Ser Asp Leu Gln Val Ala Gly Leu Phe Phe Ala
            20                  25                  30 atc ggt cac gag ccg gcg aca aaa ttt ctt gga ggg cag ctc gag ctc     144
Ile Gly His Glu Pro Ala Thr Lys Phe Leu Gly Gly Gln Leu Glu Leu
        35                  40                  45 gac tct gat ggg tat gtg gtg ccc aag ccc ggt tcc acg cac acc agt     192
Asp Ser Asp Gly Tyr Val Val Pro Lys Pro Gly Ser Thr His Thr Ser
50                  55                  60 gtg cag ggg gtc ttt gca gct ggg gat gtc cag gac aag aag tac cgc     240
Val Gln Gly Val Phe Ala Ala Gly Asp Val Gln Asp Lys Lys Tyr Arg
65                  70                  75                  80 cag gcc att act gca gct gga tca ggt tgc atg gct gct ctg gat gca     288
Gln Ala Ile Thr Ala Ala Gly Ser Gly Cys Met Ala Ala Leu Asp Ala
            85                  90                  95 gag cac tac ctg cag gag gtt gga gca cag gaa ggg aag acc gat tga     336
Glu His Tyr Leu Gln Glu Val Gly Ala Gln Glu Gly Lys Thr Asp
            100                 105                 110 ctatgtctgg gccaagctgc tcttgggcca aggaaaactt ctccgaaagc cgctctctag     396
tggtgtaaac agcacattat tatttggttt taggcctcaa attacgttac attggaaatt     456
gatttatatg agcgtgcgca agcttgtata cattattcgc attgtttatt actcttagag     516
tcttagtcat taatcacact ttgctaaaaa aaaaaaaaa                             556

<210> SEQ ID NO 23
<211> LENGTH: 111
<212> TYPE: PRT
<213> ORGANISM: Zea mays

<400> SEQUENCE: 23

Gly Gly Ala Asp Gly Gly Pro Leu Ala Gly Val Lys Val Lys Asp Val
1               5                   10                  15

Val Thr Gly Glu Val Ser Asp Leu Gln Val Ala Gly Leu Phe Phe Ala
            20                  25                  30

Ile Gly His Glu Pro Ala Thr Lys Phe Leu Gly Gly Gln Leu Glu Leu
        35                  40                  45

Asp Ser Asp Gly Tyr Val Val Pro Lys Pro Gly Ser Thr His Thr Ser
50                  55                  60

Val Gln Gly Val Phe Ala Ala Gly Asp Val Gln Asp Lys Lys Tyr Arg
65                  70                  75                  80

Gln Ala Ile Thr Ala Ala Gly Ser Gly Cys Met Ala Ala Leu Asp Ala
            85                  90                  95

Glu His Tyr Leu Gln Glu Val Gly Ala Gln Glu Gly Lys Thr Asp
            100                 105                 110

<210> SEQ ID NO 24
<211> LENGTH: 1336
<212> TYPE: DNA
<213> ORGANISM: Zea mays
<220> FEATURE:
<221> NAME/KEY: CDS
<222> LOCATION: (91)..(1086)

<400> SEQUENCE: 24
gaactgtaat tcagatttc agagcgcgca agaaccctct tgaccaccgc cgccgccgcc      60
gcgaagccaa gccaaactga gtaagcagct atg gag gga tcc gcc gcc gct ccg    114
```

```
                Met Glu Gly Ser Ala Ala Ala Pro
                  1               5 ctc cgc acg cgc atc tgc atc atc ggg agc ggt ccc gct gcg cac acg     162
Leu Arg Thr Arg Ile Cys Ile Ile Gly Ser Gly Pro Ala Ala His Thr
     10              15              20 gca gcc atc tac gcg gcc cgc gcg gag ctc aag cct gtg ctc ttc gag     210
Ala Ala Ile Tyr Ala Ala Arg Ala Glu Leu Lys Pro Val Leu Phe Glu
 25              30              35              40 ggc tgg atg gcc aac gac atc gcc gcg ggg cag ctc acc acc acc         258
Gly Trp Met Ala Asn Asp Ile Ala Ala Gly Gln Leu Thr Thr Thr
                 45              50              55 acc gac gtc gag aac ttc ccg ggc ttc ccc aac ggc atc atg ggc gcc     306
Thr Asp Val Glu Asn Phe Pro Gly Phe Pro Asn Gly Ile Met Gly Ala
             60              65              70 gac ctc atg gac aac tgc cgc gcg cag tcc ctg cgc ttt ggc acc aac     354
Asp Leu Met Asp Asn Cys Arg Ala Gln Ser Leu Arg Phe Gly Thr Asn
         75              80              85 atc ctc tcc gag acc gtc acc gcc gtc gac ttt tcg gcc tgc cca ttc     402
Ile Leu Ser Glu Thr Val Thr Ala Val Asp Phe Ser Ala Cys Pro Phe
     90              95             100 cga gtt agt gca gac tcc aca acc gtc ctc gcc gat gcg gtt atc gtt     450
Arg Val Ser Ala Asp Ser Thr Thr Val Leu Ala Asp Ala Val Ile Val
105             110             115             120 gcc acg gga gcc gtc gcg cgg cgc ctc cac ttc ccc ggg tcc gat gca     498
Ala Thr Gly Ala Val Ala Arg Arg Leu His Phe Pro Gly Ser Asp Ala
             125             130             135 tac tgg aac cgc ggc atc tcc gcc tgt gcc gtc tgt gac ggt gcc gcc     546
Tyr Trp Asn Arg Gly Ile Ser Ala Cys Ala Val Cys Asp Gly Ala Ala
         140             145             150 ccc atc ttc cgt aac aag ccc atc gcc gtc ata ggc ggc ggc gac tcc     594
Pro Ile Phe Arg Asn Lys Pro Ile Ala Val Ile Gly Gly Gly Asp Ser
     155             160             165 gct atg gag gag tcc aat ttc ctc acc aag tac ggc tcc cac gtc tac     642
Ala Met Glu Glu Ser Asn Phe Leu Thr Lys Tyr Gly Ser His Val Tyr
170             175             180 atc atc cac cgc cgc aat acc ttc cgt gct tcc aag atc atg cag gcc     690
Ile Ile His Arg Arg Asn Thr Phe Arg Ala Ser Lys Ile Met Gln Ala
185             190             195             200 agg gcg ctt gag aac ccc aaa att aag gtc ctc tgg gac tcg gaa gtt     738
Arg Ala Leu Glu Asn Pro Lys Ile Lys Val Leu Trp Asp Ser Glu Val
             205             210             215 gtc gag gcc tat ggc ggc gca aac ggc ggc cca ttg gct ggc gta aag     786
Val Glu Ala Tyr Gly Gly Ala Asn Gly Gly Pro Leu Ala Gly Val Lys
         220             225             230 gtt aag aac cta ctg aat ggt gag gtc tcg gat ctt cag gtg tct ggc     834
Val Lys Asn Leu Leu Asn Gly Glu Val Ser Asp Leu Gln Val Ser Gly
     235             240             245 ctc ttc ttc gcc atc ggg cat gag ccg gcg acc aaa ttc ctg ggc gga     882
Leu Phe Phe Ala Ile Gly His Glu Pro Ala Thr Lys Phe Leu Gly Gly
250             255             260 cag ctt gaa ctc gat tca gat ggt tat gtg gaa acc aag cca ggt tcc     930
Gln Leu Glu Leu Asp Ser Asp Gly Tyr Val Glu Thr Lys Pro Gly Ser
265             270             275             280 act cac acc agt gta aag ggt gta ttt gct gct ggc gac gtg cag gac     978
Thr His Thr Ser Val Lys Gly Val Phe Ala Ala Gly Asp Val Gln Asp
             285             290             295 aag aag tac cgt cag gcc att act gcc gct gga tca ggg tgc atg gct    1026
Lys Lys Tyr Arg Gln Ala Ile Thr Ala Ala Gly Ser Gly Cys Met Ala
300             305             310
```

```
gca ttg gac gct gag cac tac ctg cag gag atc ggt gca cag gag gga    1074
Ala Leu Asp Ala Glu His Tyr Leu Gln Glu Ile Gly Ala Gln Glu Gly
        315                 320                 325 aag tct gat tga ctatatttag gtgtagcaac cagcaatcca tcgaatagtc         1126
Lys Ser Asp
    330 agttgtcggt gctgaaagcc gctctctgat gcgcgtttat gccatgggtt gtcatgagct   1186 cacgattgag atacctgatg atttatgctg cttagtagca tgctattctt atcgttagga   1246 tccagaagta tgtctgaact ctgaactatt tactggatac ctattcgtga ttactgcctt   1306 gaagttttc cttagatatc aaaaaaaaaa                                     1336
```

<210> SEQ ID NO 25
<211> LENGTH: 331
<212> TYPE: PRT
<213> ORGANISM: Zea mays

<400> SEQUENCE: 25

```
Met Glu Gly Ser Ala Ala Ala Pro Leu Arg Thr Arg Ile Cys Ile Ile
1               5                   10                  15

Gly Ser Gly Pro Ala Ala His Thr Ala Ala Ile Tyr Ala Ala Arg Ala
            20                  25                  30

Glu Leu Lys Pro Val Leu Phe Glu Gly Trp Met Ala Asn Asp Ile Ala
        35                  40                  45

Ala Gly Gly Gln Leu Thr Thr Thr Thr Asp Val Glu Asn Phe Pro Gly
    50                  55                  60

Phe Pro Asn Gly Ile Met Gly Ala Asp Leu Met Asp Asn Cys Arg Ala
65                  70                  75                  80

Gln Ser Leu Arg Phe Gly Thr Asn Ile Leu Ser Glu Thr Val Thr Ala
                85                  90                  95

Val Asp Phe Ser Ala Cys Pro Phe Arg Val Ser Ala Asp Ser Thr Thr
            100                 105                 110

Val Leu Ala Asp Ala Val Ile Val Ala Thr Gly Ala Val Ala Arg Arg
        115                 120                 125

Leu His Phe Pro Gly Ser Asp Ala Tyr Trp Asn Arg Gly Ile Ser Ala
    130                 135                 140

Cys Ala Val Cys Asp Gly Ala Ala Pro Ile Phe Arg Asn Lys Pro Ile
145                 150                 155                 160

Ala Val Ile Gly Gly Gly Asp Ser Ala Met Glu Glu Ser Asn Phe Leu
                165                 170                 175

Thr Lys Tyr Gly Ser His Val Tyr Ile Ile His Arg Arg Asn Thr Phe
            180                 185                 190

Arg Ala Ser Lys Ile Met Gln Ala Arg Ala Leu Glu Asn Pro Lys Ile
        195                 200                 205

Lys Val Leu Trp Asp Ser Glu Val Val Glu Ala Tyr Gly Gly Ala Asn
    210                 215                 220

Gly Gly Pro Leu Ala Gly Val Lys Val Lys Asn Leu Leu Asn Gly Glu
225                 230                 235                 240

Val Ser Asp Leu Gln Val Ser Gly Leu Phe Ala Ile Gly His Glu
                245                 250                 255

Pro Ala Thr Lys Phe Leu Gly Gly Gln Leu Glu Leu Asp Ser Asp Gly
            260                 265                 270

Tyr Val Glu Thr Lys Pro Gly Ser Thr His Thr Ser Val Lys Gly Val
        275                 280                 285

Phe Ala Ala Gly Asp Val Gln Asp Lys Lys Tyr Arg Gln Ala Ile Thr
```

-continued

```
                  290                 295                 300
Ala Ala Gly Ser Gly Cys Met Ala Ala Leu Asp Ala Glu His Tyr Leu
305                 310                 315                 320

Gln Glu Ile Gly Ala Gln Glu Gly Lys Ser Asp
                325                 330
```